US010709521B2

(12) United States Patent
Hansen et al.

(10) Patent No.: US 10,709,521 B2
(45) Date of Patent: Jul. 14, 2020

(54) METHOD AND APPARATUS TO ACCOUNT FOR TRANSPONDER TAGGED OBJECTS USED DURING CLINICAL PROCEDURES, EMPLOYING A SHIELDED RECEPTACLE

(71) Applicant: Covidien LP, Mansfield, MA (US)

(72) Inventors: Bryan Hansen, Galway (IE); Jeffrey Jensen, Boulder, CO (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 16/316,986

(22) PCT Filed: Jul. 7, 2017

(86) PCT No.: PCT/US2017/041028
§ 371 (c)(1),
(2) Date: Jan. 10, 2019

(87) PCT Pub. No.: WO2018/013411
PCT Pub. Date: Jan. 18, 2018

(65) Prior Publication Data
US 2019/0290392 A1    Sep. 26, 2019

Related U.S. Application Data

(60) Provisional application No. 62/360,864, filed on Jul. 11, 2016.

(51) Int. Cl.
*A61B 90/98* (2016.01)
*G16H 40/20* (2018.01)
(Continued)

(52) U.S. Cl.
CPC .......... *A61B 90/98* (2016.02); *G06K 7/10356* (2013.01); *G06K 7/10396* (2013.01);
(Continued)

(58) Field of Classification Search
None
See application file for complete search history.

(56) References Cited

U.S. PATENT DOCUMENTS 4,215,796 A * 8/1980 Johnston .............. B65D 50/067
174/377
5,610,811 A    3/1997 Honda
(Continued)

OTHER PUBLICATIONS

International Search Report and Written Opinion corresponding to counterpart Int'l Appln. No. PCT/US2017/041028 dated Nov. 9, 2017.

(Continued)

*Primary Examiner* — Thomas S McCormack
(74) *Attorney, Agent, or Firm* — Carter, DeLuca & Farrell LLP

(57) ABSTRACT

Medical procedure related objects (e.g., instruments, supplies) tagged with transponders (e.g., RFID transponders, dumb transponders) are accounted for in a medical or clinical environment via an accounting system using a number of antennas and interrogators/readers. A first set of antennas and RFID interrogator(s) interrogate portions of the environment for RFID tagged objects, for example proximate a start and an end of a procedure. Shielded packaging and/or shielded receptacles shield tagged objects, preventing interrogation except for those objects in unshielded portions of the environment. A shielded receptacle may include an antenna to interrogate the contents thereof in a relatively noise-free environment. A data store may maintain information including a current status or count of each instrument or supply, for instance as checked in or checked out. A handheld antenna and/or second set of antennas interrogates a body of a patient for retained instruments or supplies tagged with dumb transponders.

13 Claims, 18 Drawing Sheets

(51) Int. Cl.
*G06K 7/10* (2006.01)
*G06K 19/07* (2006.01)
*A61B 90/00* (2016.01)
*G16H 10/65* (2018.01)

(52) U.S. Cl.
CPC ......... *G06K 19/0723* (2013.01); *G16H 40/20* (2018.01); *A61B 2090/0805* (2016.02); *G06K 7/10386* (2013.01); *G16H 10/65* (2018.01)

(56) References Cited

U.S. PATENT DOCUMENTS

| | | | |
|---|---|---|---|
| 6,026,818 A | 2/2000 | Blair et al. | |
| 6,650,143 B1 | 11/2003 | Peng | |
| 6,667,902 B2 | 12/2003 | Peng | |
| 6,671,040 B2 | 12/2003 | Fong et al. | |
| 6,700,151 B2 | 3/2004 | Peng | |
| 6,766,960 B2 | 7/2004 | Peng | |
| 6,777,757 B2 | 8/2004 | Peng et al. | |
| 6,791,891 B1 | 9/2004 | Peng et al. | |
| 6,798,693 B2 | 9/2004 | Peng | |
| 6,822,888 B2 | 11/2004 | Peng | |
| 6,856,540 B2 | 2/2005 | Peng et al. | |
| 6,898,116 B2 | 5/2005 | Peng | |
| 6,940,751 B2 | 9/2005 | Peng et al. | |
| 6,956,258 B2 | 10/2005 | Peng | |
| 6,972,986 B2 | 12/2005 | Peng et al. | |
| 6,992,925 B2 | 1/2006 | Peng | |
| 7,031,209 B2 | 4/2006 | Wang et al. | |
| 7,042,722 B2 | 5/2006 | Suzuki et al. | |
| 7,269,047 B1 | 9/2007 | Fong et al. | |
| 7,471,541 B2 | 12/2008 | Fong et al. | |
| 7,482,925 B2 * | 1/2009 | Hammad | G06K 19/005 174/377 |
| 7,609,538 B1 | 10/2009 | Lee et al. | |
| 7,696,877 B2 | 4/2010 | Barnes et al. | |
| 7,898,420 B2 | 3/2011 | Blair et al. | |
| 8,105,296 B2 | 1/2012 | Morris et al. | |
| 8,111,162 B2 | 2/2012 | Barnes et al. | |
| 8,181,860 B2 | 5/2012 | Fleck et al. | |
| 8,193,938 B2 | 6/2012 | Halberthal et al. | |
| 8,354,931 B2 | 1/2013 | Blair | |
| 8,358,212 B2 | 1/2013 | Blair | |
| 8,710,957 B2 | 4/2014 | Blair et al. | |
| 9,136,597 B2 | 9/2015 | Blair | |
| 9,514,341 B2 | 12/2016 | Blair et al. | |
| 9,592,962 B1 | 3/2017 | Lee | |
| 9,690,963 B2 | 6/2017 | Buhler et al. | |
| 9,717,565 B2 | 8/2017 | Blair | |
| 9,872,732 B2 | 1/2018 | Blair | |
| 10,193,209 B2 | 1/2019 | Blair | |
| 2004/0250819 A1 | 12/2004 | Blair et al. | |
| 2007/0285249 A1 | 12/2007 | Blair et al. | |
| 2010/0108079 A1 * | 5/2010 | Blair | G06K 19/04 128/899 |
| 2010/0109848 A1 | 5/2010 | Blair et al. | |
| 2011/0004276 A1 | 1/2011 | Blair et al. | |
| 2011/0181394 A1 | 7/2011 | Blair | |
| 2012/0169470 A1 * | 7/2012 | Lee | G06K 19/07749 340/10.1 |
| 2013/0016021 A1 | 1/2013 | Blair | |
| 2014/0303580 A1 | 10/2014 | Blair | |
| 2015/0272688 A1 | 10/2015 | Blair et al. | |
| 2015/0363618 A1 | 12/2015 | Fleck et al. | |
| 2016/0210548 A1 | 7/2016 | Blair | |
| 2016/0250000 A1 | 9/2016 | Blair | |
| 2017/0169172 A1 | 6/2017 | Blair et al. | |

OTHER PUBLICATIONS

U.S. Appl. No. 62/182,294, filed Jun. 19, 2015.
U.S. Appl. No. 62/164,412, filed May 20, 2015.

* cited by examiner

METHOD AND APPARATUS TO ACCOUNT FOR TRANSPONDER TAGGED OBJECTS USED DURING CLINICAL PROCEDURES, EMPLOYING A SHIELDED RECEPTACLE

CROSS-REFERENCE TO RELATED APPLICATIONS

This application is a U.S. National Stage Application filed under 35 U.S.C. § 371(a) of International Patent Application Serial No. PCT/US2017/041028, filed Jul. 7, 2017, which claims the benefit of and priority to U.S. Provisional Patent Application Ser. No. 62/360,864, filed Jul. 11, 2016, the entire disclosures of which are incorporated by reference herein.

BACKGROUND

Technical Field

The present disclosure generally relates to a wireless medical procedure environment, and, more particularly, accounting for transponder tagged medical or clinical procedure objects or items, for instance disposable gauze or sponges, and/or medical or clinical instruments typically employed in a medical or clinical environment in which medical or clinical procedures are performed.

Description of the Related Art

It is important to determine whether objects or items associated with a medical or clinical procedure are present or unintentionally retained in a patient's body before completion of a medical or clinical procedure. The medical or clinical procedure may, for example, take the form of a surgery or childbirth delivery. Such objects or items may take a variety of forms used in medical or clinical procedures. For example, the objects or items may take the form of instruments, for instance scalpels, scissors, forceps, hemostats, and/or clamps, which may be reusable after sterilization or alternatively may be single-use disposable objects or items. Also for example, the objects or items may take the form of related accessories and/or disposable objects, for instance disposable surgical sponges, gauzes, and/or absorbent pads. When used in surgery, failure to locate an object or item before closing the patient may require additional surgery, and in some instances may have serious adverse medical consequences. In other medical procedures, such as vaginal childbirth deliveries, failure to remove objects, for instance gauze or absorbent pads, can lead to infections and undesired complications.

Some hospitals have instituted procedures that include checklists or requiring multiple manual counts to be performed to track the use and return of objects or items during surgery. Such a manual approach is inefficient, requiring the time of highly trained personnel, and is prone to error.

Another approach employs wireless transponders that are attached to various objects or items used during surgery, and a wireless interrogation and detection system. Such an approach can employ "dumb" wireless transponders, i.e., wireless communications transponders that do not store and/or transmit any unique identifying information. Dumb wireless transponders have traditionally been employed for electronic article surveillance (EAS) to prevent loss of merchandise at retail locations. Alternatively, such an approach can employ radio frequency identification (RFID) wireless transponders, i.e., wireless communications transponders which do store and return a unique identifier in response to an interrogation signal emitted by an RFID interrogator or RFID reader.

In the approach that employs dumb wireless transponders, an interrogation and detection system includes a transmitter that emits pulsed wireless interrogation signals (e.g., radio or microwave frequency) and a detector for detecting wireless response signals returned by the dumb wireless transponders in response to the emitted interrogation signals. Such an automated system detects the presence or absence of dumb wireless transponders, but typically does not detect any unique identifying information. Since no power is required to operate the dumb wireless transponder, such an approach may have better range or better ability to detect objects or items retained within bodily tissue as compared to RFID wireless transponders communicating in similar ranges of wavelength and levels of power, but cannot uniquely identify the dumb wireless transponders. Examples of such an approach are discussed in U.S. Pat. No. 6,026,818, issued Feb. 22, 2000, and U.S. Patent Publication No. US 2004/0250819, published Dec. 16, 2004.

In the approach that employs RFID wireless transponders, an interrogator or reader includes a transmitter that emits wireless interrogation signals (e.g., radio or microwave frequency) and a detector for detecting wireless response signals returned by the RFID wireless transponders in response to the emitted interrogation signals. Such an automated system advantageously detects the unique identifiers of the RFID wireless transponders; however since some of the power in the interrogation signal is required to operate the RFID wireless transponder such an approach may have shorter range or less ability to detect objects or items retained within bodily tissue as compared to dumb wireless transponders communicating in similar ranges of wavelength and levels of power. Examples of such an approach are discussed in U.S. Pat. Nos. 8,105,296; 8,181,860; and U.S. Patent Application Publication No. 2015/0363618.

Commercial implementation of such an automated system requires that the overall system be cost competitive, highly accurate, and easy to use. In particular, false negatives must be avoided to ensure that objects are not mistakenly left in the patient and false positives avoided to ensure valuable time and resources are not spent looking for objects which were not actually retained in the patient. Consequently, a new approach to prevention of foreign object retention in medical procedure environments is highly desirable.

BRIEF SUMMARY

A system to track items in a clinical environment may be summarized as including a number of antennas, the antennas positioned and oriented in the clinical environment to provide coverage of the clinical environment; at least one interrogator, the at least one interrogator communicatively coupled to the antennas and operable to cause the at least one antenna to emit at least one of radio or microwave frequency energy interrogation signals and to detect response signals from any exposed wireless communications transponders in the clinical environment; and at least one shielded receptacle in the clinical environment, the at least one shielded receptacle having an interior and at least one shield that shields the interior of the shielded receptacle and any wireless communications transponders in the interior from at least one of radio or microwave frequency energy emitted by the antennas, at least one of the at least one shielded receptacle is in a closed configuration.

The system may further include a plurality of tagged clinical procedure items, each of the tagged items clinical procedure items having a respective wireless communications transponder physically coupled thereto.

The system may further include at least one piece of packaging, the at least one piece of packaging having an interior and at least one shield that shields the interior of the packaging and any wireless communications transponders in the interior of the packaging from at least one of radio or microwave frequency energy emitted by the antennas while the at least one piece of packaging is sealed, wherein the at least one piece of packaging releasably retains a number of the tagged clinical procedure items prior to use of the tagged clinical procedure items. At least one of the at least one piece of packaging may include a disposable metal or metalized foil envelope. The tagged clinical procedure items may be disposable pieces of gauze and at least one of the at least one piece of packaging may contain at least two sterile tagged disposable pieces of gauze prior to opening of the respective piece of packaging and the at least one of the at least one piece of packaging may be hermetically sealed prior to opening of the respective piece of packaging. At least one of the at least one piece of packaging may include a disposable or a re-sterilizable tray or tote. The plurality of tagged clinical procedure items may include a number of tagged disposable items, each of the tagged disposable items having a respective radio frequency identification (RFID) wireless communications transponder physically coupled thereto. The plurality of tagged clinical procedure items may include a number of tagged clinical procedure instruments, each of the tagged clinical procedure instruments having a respective radio frequency identification (RFID) wireless communications transponder physically coupled thereto.

The system may further include at least one processor, the at least one processor communicatively coupled to the at least one interrogator; and at least one nontransitory processor-readable medium that stores at least one of processor-executable instructions or data, execution of which causes the at least one processor to: proximate an end of a clinical procedure, determine whether the at least one antenna in the clinical environment detected any response signals from any wireless transponders in the clinical environment.

The at least one of processor-executable instructions or data, when executed may further cause the at least one processor to cause an alert to be provided in response to a determination that the at least one antenna detected at least one response signals from any wireless transponders in the clinical environment proximate the end of the clinical procedure. The at least one of processor-executable instructions or data, when executed may cause the at least one processor to determine whether the at least one antenna in the clinical environment detected any response signals from any wireless transponders proximate the end of the clinical procedure without determining whether any wireless transponders are present in the shielded receptacle. The at least one shielded receptacle may have a port that may be selectively operable between the closed configuration and an open configuration, in the open configuration the port may provide physical access to the interior of the shielded receptacle from an exterior thereof and in the closed configuration the port may prevent physical access to the interior of the shielded receptacle from the exterior thereof. The port of the at least one shielded receptacle may include a cover selectively moveable between the closed configuration and the open configuration. The cover may be biased into the closed configuration. The at least one antenna may include a plurality of room antennas, positioned throughout the clinical environment, and oriented to provide coverage of substantially all unshielded portions of the clinical environment.

A method of operation of a system to track items in a clinical environment may be summarized as including during a first period, causing at least one antenna to emit at least one interrogation signal, the antennas positioned and oriented to provide coverage of any unshielded portions of the clinical environment; during the first period, detecting any response signals to the at least one interrogation signal, the response signals returned from any wireless transponders in the unshielded portions of the clinical environment; identifying, by the at least one processor, each of a number of wireless transponders in the unshielded portions of the clinical environment based on the response signals detected during the first period; adding a number of item entries to an inventory stored to at least one nontransitory processor-readable medium based at least in part on the response signals detected during the first period, each of the item entries in the inventory representative of a respective items prepared for use during a clinical procedure; during a second period, causing the at least one antenna to emit at least one interrogation signal; during the second period, detecting any response signals to the at least one interrogation signal, the response signals including at least one response signal returned from at least one wireless transponders that was removed from a shielded package between the first and the second periods; identifying, by the at least one processor, each of a number of wireless transponders in the unshielded portions of the clinical environment based on the response signals detected during the second period; and updating the inventory based on the response signals detected during the second period, including adding at least one item entry to the inventory that corresponds to the at least one wireless transponders that was removed from a shielded package between the first and the second periods.

The method may further include during a third period proximate an end of a clinical procedure, causing the at least one room antenna to emit at least one interrogation signal; during the third period, detecting any response signals to the at least one interrogation signal; identifying, by the at least one processor, each of a number of wireless transponders in the unshielded portions of the clinical environment based on the response signals detected during the third period; and updating the inventory based on the response signals detected during the third period. Updating the inventory based on the response signals detected during the third period may include at least one of adding an item entry or updating a status of an item entry in the inventory.

Causing, during the first or the third period, at least one antenna to emit at least one interrogation signal may include causing a plurality of room antennas to emit interrogation signals, the room antennas positioned and oriented to provide coverage of any unshielded portions of the clinical environment.

An article for use in clinical environments may be summarized as including at least one clinical procedure item; at least one wireless communications transponder physically coupled to a respective one of the at least one clinical procedure item; and at least one piece of packaging, the at least one piece of packaging having an interior and comprising at least one shield that completely shields the interior of the packaging and any wireless communications transponders in the interior of the packaging from at least one of radio or microwave frequency energy emitted from an exterior of the packaging while the at least one piece of packaging is sealed, at least one clinical procedure item and the at least one wireless communications transponder releasably retained by the at least one piece of packaging prior to use of the at least one clinical procedure item. The at least one piece of packaging may include a disposable envelope. The disposable envelope may include a metalized foil envelope. The at least one piece of packaging may include a metal grid or metalized foil grid that completely surrounds the at least one clinical procedure item and the at least one wireless communications transponder may be releasably retained by the at least one piece of packaging prior to use of the at least one clinical procedure item. The at least one clinical procedure item may include at least one piece of disposable gauze. The at least one piece of packaging may include a tray or a tote with a selectively removable cover. The tray or the tote may be metal. The tray or the tote may include a polymer shell with a metal cages. The tray or the tote may be reusable and re-sterilizable packaging. The selectively removable cover may be a metalized foil cover. The selectively removable metalized foil cover may not be re-sterilizable. The at least one clinical procedure item may include at least one piece of disposable gauze. The at least one clinical procedure item may include at least one clinical procedure instrument. The at least one wireless communications transponder physically coupled to a respective one of the at least one disposable item may include at least one radio frequency identification (RFID) wireless communications transponder physically coupled to the respective one of the at least one disposable item. The interior of the at least one piece of packaging may be hermetically sealed with respect to the exterior of the packaging prior to opening of the packaging and the at least one disposable item and the at least one wireless communications transponder may be releasably retained by the at least one piece of packaging are sterile prior to opening of the respective piece of packaging. The at least one piece of packaging may contain at least two disposable items prior to opening of the respective piece of packaging, each of the at least two items physically coupled to a respective wireless communications transponder. A first one the at least one piece of packaging may contain at least two disposable sterile pieces gauze prior to opening of the piece of packaging, each of the at least two disposable sterile pieces gauze physically coupled to a respective wireless communications transponder. The at least one wireless communications transponder may include at least one passive radio frequency identification (RFID) transponder. The at least one piece of packaging may bear at least one machine-readable symbol on an exterior thereof, the at least one machine-readable symbol which encodes information that identifies at least a manufacturer or lot to which the respective piece of packaging or disposable items belongs. The at least one piece of packaging at least one wireless transponder may be physically attached to the piece of packaging and not physically attached to any of the at least one disposable item, the at least one wireless transponder which stores information that identifies at least a manufacturer or lot to which the respective piece of packaging or disposable items belongs.

BRIEF DESCRIPTION OF THE SEVERAL
VIEWS OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

FIG. 1 is an isometric view of a medical or clinical environment in which a medical or clinical procedure is performed, according to one illustrated implementation, and which includes a patient support structure, a table or stand on which medical or clinical procedure instruments and supplies are carried, a receptacle to collect medical or clinical procedure instruments and supplies, a plurality of antennas and a radio frequency identification interrogator, an accounting system communicatively coupled to the interrogators, a number of antennas and a dumb transponder interrogator, a number of pieces of medical or clinical procedure objects or items and associated packaging which may advantageously shield the medical or clinical procedure objects or items until opened.

FIG. 2A is an isometric view of a piece of shielded packaging in the form of a shielded envelope or shielded pouch shown in an unopened configuration, the piece of shielded packaging which contains or holds one or more medical or clinical objects or items, each of which includes one or more wireless communications transponders, according to at least one illustrated implementation, the shielded packaging which prevents the wireless communications transponders from receiving interrogations signals and/or responding to interrogations signals at least until the shielded packaging is opened.

FIG. 2B is an isometric view of the shielded envelope of FIG. 2A shown in an opened configuration, along with a number of medical or clinical objects or items which have been removed from the piece of shielded packaging, and which each includes one or more wireless communications RFID transponders and/or one or more wireless communications dumb transponders, according to at least one illustrated implementation.

FIG. 2C is an exploded isometric view of the shielded envelope or shielded pouch of FIGS. 2A and 2B, which, according to at least one illustrated implementation, can include a packaging layer, a foil shield layer, and which itself may carry or bear a label with identifying information, and/or one or more wireless communications RFID transponders and/or one or more wireless communications dumb transponders.

FIG. 2D is an exploded isometric view of the shielded envelope or shielded pouch of FIGS. 2A and 2B, which, according to at least one illustrated implementation, can include a packaging layer, an electrically conductive mesh or grid shield layer, and which itself may carry or bear a label with identifying information, and/or one or more wireless communications RFID transponders and/or one or more wireless communications dumb transponders.

FIG. 3A is an isometric view of the piece of shielded packaging in the form of a shielded tote or tray shown in an unopened configuration, the piece of shielded packaging which contains or holds one or more medical or clinical objects or items, each of which includes one or more wireless communications transponders, according to at least one illustrated implementation, the shielded packaging which prevents the wireless communications transponders from receiving interrogations signals and/or responding to interrogations signals at least until the shielded packaging is opened.

FIG. 3B is an isometric view of the shielded tote or tray of FIG. 3A shown in an opened configuration along with a number of medical or clinical objects or items which have been removed from the piece of shielded packaging, and which each includes one or more wireless communications RFID transponders and/or one or more wireless communications dumb transponders, according to at least one illustrated implementation.

Figure 1:
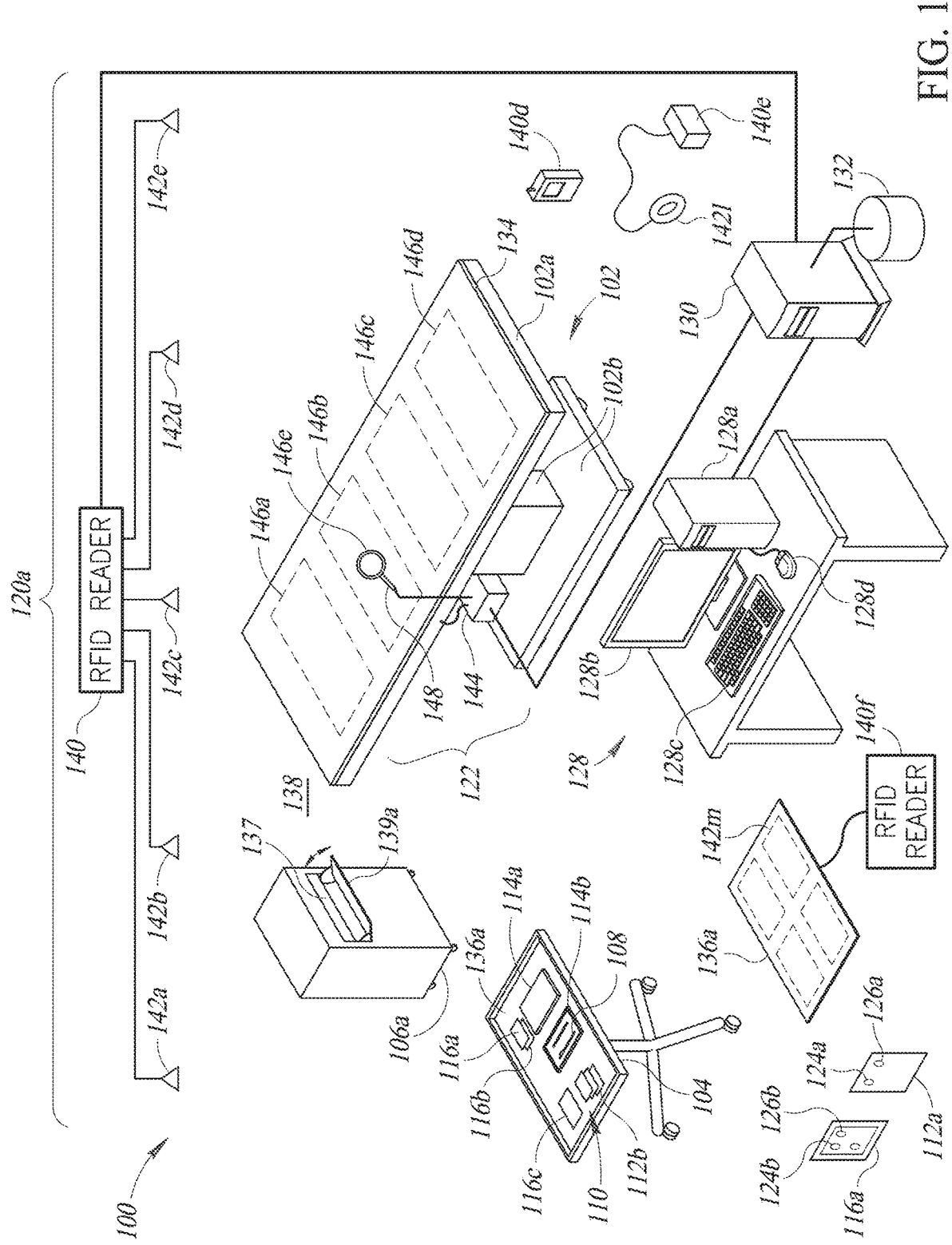

FIGS. 11A-11F are a flow diagram showing a workflow or method of operation in a medical or clinical environment according to at least one implementation, employing various of the apparatus or devices described in reference to FIGS. 1-10, and particularly suited to be implemented by the structures of FIG. 1, which includes one or more receptacles without receptacle RFID interrogators or readers, and optionally includes interrogating for a presence or absence of dumb transponders in a body of a patient.

DETAILED DESCRIPTION

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with transmitters, receivers, or transceivers and/or medical equipment and medical facilities have not been shown or described in detail to avoid unnecessarily obscuring descriptions of the embodiments.

Unless the context requires otherwise, throughout the specification and claims which follow, the word "comprise" and variations thereof, such as "comprises" and "comprising," are to be construed in an open, inclusive sense, that is as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The headings and Abstract of the Disclosure provided herein are for convenience only and do not interpret the scope or meaning of the embodiments.

FIG. 1 shows a medical or clinical environment 100 in which a medical or clinical procedures are performed, according to one illustrated implementation.

The medical or clinical procedure environment 100 may take any of a variety of forms, for example a surgical environment or operating room in which surgeries are performed, or an emergency room (ER) in which various medical or clinical procedures are performed. Other medical or clinical procedure environments 100 may take the form of a patient room, examination room or physician's office, etc., in which medical or clinical procedures are performed, or a dedicated labor and delivery (L&D) room in which vaginal child birth or deliveries are performed.

The medical or clinical procedure environment 100 typically includes a patient support structure 102 that can carry a patient (not shown) or portion thereof. The medical procedure environment 100 typically includes a number of accessory tables or stands 104 (only one shown in FIG. 1), for example to hold medical or clinical procedure instruments 108 (one shown) and/or supplies 110. The medical or clinical procedure environment 100 may include one or more receptacles 106a, for example to collect used medical or clinical procedure instruments 108 and/or supplies 110. As discussed in detail below, the receptacle(s) 106a may advantageously shield (e.g., Faraday cage) the contents of the receptacle(s) 106a from wireless communications (e.g., radio frequencies, microwave frequencies) at least while the receptacle(s) 106a is in a closed configuration.

The medical or clinical procedure environment 100 will typically include one or more medical or clinical procedure related objects or items, for example one or more implements or instruments 108 (only one shown) and one or more supplies 110. As a non-limiting example, instruments 108 may take the form of scalpels, scissors, forceps, hemostats, clamps, retractors, and/or trocars. As a non-limiting example, supplies 110 may take the form of disposable or reusable supplies, and for instance, sponges (e.g., surgical sponges), gauze and/or padding 112a, 112b (only two called out in FIG. 1, collectively 112).

The medical or clinical procedure environment 100 may include one or more totes or trays 114a, 114b (two shown, collectively 114) that carry instruments 108 and/or supplies 110. The totes or trays 114 may be hermetically sealed (e.g., tote or tray 114a) until opened (e.g., tote or tray 114b) for use, in order to maintain the contents of the totes or trays 114 sterile prior to introduction of the contents into the medical or clinical procedure environment 100 for use. As discussed in detail below, the totes or trays 114 may advantageously shield (e.g., Faraday cage) the contents of the totes or trays 114 from wireless communications (e.g., radio frequencies, microwave frequencies) at least until the totes or trays 114 are opened and/or the contents removed from the totes or trays 114.

The medical or clinical procedure environment 100 may include one or more pieces of packaging 116a, 116b, 116c (e.g., packets, envelopes or sleeves, three shown, collectively 116) which carry instruments 108 and/or supplies 110. The packaging 116 may be hermetically sealed (e.g., packets or envelopes 116a, 116b) until opened (e.g., packet or envelope 116c) for use, to maintain the contents of the packaging sterile prior to introduction into the medical or clinical procedure environment 100 for use. The packaging 116 may, for example, take the form of hermetically sealed packets or envelopes 116a, 116b that enclose a number of sponges (e.g., surgical sponges), gauze and/or padding 112. As discussed in detail below, the packaging 116 may advantageously shield (e.g., Faraday cage) the contents of the packaging 116 from wireless communications (e.g., radio frequencies, microwave frequencies) at least until the packaging 116 is opened and/or the contents removed from the packaging 116.

The medical or clinical procedure related instruments or implements 108 and/or supplies 110, totes or trays 114 and/or packaging 116 are typically held, supported or carried by the tables or stands 104 when not in use.

As illustrated and described elsewhere herein, one or more implements or instruments 108 and/or one or more supplies 110 may have one or more wireless communications transponders physically attached thereto. As illustrated and described elsewhere herein, for example one or more trays or totes 114 and/or one or more pieces of packaging 116 may have one or more wireless communications transponders physically attached thereto.

The medical or clinical procedure environment 100 will typically include one or more pieces of medical or clinical procedure related equipment (not shown), for instance one or more lamps, anesthetizing equipment, heart/lung machines or cardiopulmonary bypass machines, ventilators, cauterization equipment, defibrillator, aspirator equipment, infusion pump, dialysis machine, intra-aortic balloon pump, various monitors such as blood pressure, heart or pulse rate, pulse-oxygen (pulse-ox or pulse oximetry) sensor, temperature, EKG sensors or electrodes or electrical conductivity sensors, intracranial pressure sensors, pH sensors, other dedicated medical diagnostic, therapeutic or monitoring equipment, etc. One or more of these pieces of medical or clinical procedure related equipment may be a source of electronic noise, making it difficult to identify wireless communications transponders in the medical or clinical procedure environment 100.

Where the medical procedure environment 100 is an operating room or operating theater, there will typically be a number of medical providers present. For instance, medical providers present during a surgery may include a surgeon, a first assistant surgeon, a second assistant surgeon, an anesthetist, an instrument nurse, a supply nurse, and/or one or more circulating nurses (not illustrated). The surgeons or physicians are typically responsible for working directly on a patient, for example cutting, excising, cauterizing, suturing, ablating, fastening, implanting, etc. The anesthetist is typically responsible for administering anesthesia and monitoring certain vital signs, such as blood pressure, pulse, oxygen level and/or blood gases. The instrument and supply nurses, respectively, may be responsible for handing instruments 108 and supplies 110 from the instrument and supply tables 104 to the surgeons, and collecting the instruments 108 and supplies 110 after use. Some or all of the instruments and/or supplies may be deposited in the receptacle 106a after use.

The medical procedure environment 100 may include one or more wireless communications identification interrogation systems, for example one or more radio frequency identification (RFID) interrogation systems 120a. The RFID interrogation system(s) 120a is(are) operable to interrogate wireless communications identification transponders, for example RFID transponders or RFID tags 124a, 124b (only two shown in FIG. 1, collectively 124), receive return signals from RFID transponders or RFID tags 124 which encode unique identifiers, and thereby uniquely identify the RFID transponders or RFID tags 124 within the range of the RFID interrogation system(s) 120a. The RFID transponders or RFID tags 124 store and return unique identifiers (e.g., unique at least within a large enough set to supply a large clinical facility for a month). The RFID transponders or RFID tags 124 may, preferably, take the form of passive RFID transponders or RFID tags which omit batteries and derive power for operation from the interrogation signal. While denominated as "radio frequency," commercial RFID interrogator systems 120a and RFID transponders or tags 124 typically operate or communicate in the low or high frequency (e.g., radio frequency) and/or ultra-high frequency (e.g., microwave frequency) portions of the electromagnetic spectrum. Hence, consistent with common usage in the field of automatic data collection, use of the terms radio frequency and/or RFID is not limited to interrogation systems and wireless communications transponders that employ radio frequency communications, but also include interrogation systems and wireless communications transponders that employ microwave frequency communications.

The medical procedure environment 100 may include one or more wireless communications presence/absence interrogation systems 122. The presence/absence interrogation system(s) 122 is operable to interrogate wireless communications dumb transponders 126a, 126b (only two shown in FIG. 1, collectively 126), receive return wireless communications dumb transponders 126 which do not encode unique identifiers, and determine at least one of a presence or absence of the wireless communications dumb transponders 126 in the range of the wireless communications presence/absence interrogation system(s) 122. The wireless communications dumb transponders 126 are typically simple LC resonant circuits, and do not store, encode or return unique identifiers. The wireless communications presence/absence interrogation system(s) 122 and the wireless communications dumb transponders 126 typically communicate a lower frequency range than RFID interrogator system(s) 120a and the RFID transponders or RFID tags 124. This may advantageously result in better range than obtainable by the RFID interrogator system(s) 120a, and increased ability to detect a wireless communications dumb transponder 126 retained in bodily tissue, even where a patient is obese. In some instances, the frequency range of the RFID interrogator system(s) 120a and the wireless communications presence/absence interrogation system(s) 122 does not overlap.

The medical procedure environment 100 may include one or more computers or terminals 128 to allow entry and/or access to information, for example an inventory of instruments 108 and supplies 110 for a particular medical or clinical procedure. The computers or terminals 128 can take a large variety of forms, for example a desktop computer or terminal, laptop computer, netbook computer, tablet computer, or smartphone. The computers or terminals 128 may include a computer housing 128a which houses one or more processors, one or more memories (e.g., RAM, ROM, FLASH), one or more hard disk drives, one or more solid state drives, etc. The computers or terminals 128 may include a display 128b, and one or more user input devices, for example a keyboard 128c and/or pointer device such as a computer mouse 128d.

The medical procedure environment 100 may include an accounting system 130 that is operable to maintain in a nontransitory computer- or processor-readable medium 132 an inventory of instruments 108 and supplies 110 at least for a particular medical or clinical procedure. The RFID interrogation system(s) 120a and presence/absence interrogation system(s) 122 are each communicatively coupled to the accounting system 130 via one or more wired or wireless communications channels (e.g., tethered, serial networked). The accounting system 130 can receive information autonomously generated by the RFID interrogation system(s) 120a and presence/absence interrogation system(s) 122, allowing automated itemization and inventorying functions to be performed. The computers or terminals 128 may be communicatively coupled to the accounting system 130 via one or more wired or wireless communications channels (e.g., tethered, serial networked) allowing manual entry of information, for instance manual counts of instruments 108 and/or supplies 110, as well as checking of the status of defined items or of the inventory for a given medical or clinical procedure.

The accounting system 130 may be communicatively coupled to a backend accounting or validation or inventory system (not shown), which stores information in at least one nontransitory computer- or processor-readable medium. The backend accounting or validation or inventory system may be located on the premises of the medical or clinical procedure environment 100, or located remotely therefrom. The backend accounting or validation or inventory system may be communicatively coupled to the accounting system 130 via any variety of wired or wireless communications channels including one or more networks. The backend accounting or validation or inventory system may, for example, manage inventory for multiple medical or clinical procedure environments 100. The accounting system 130 and/or the backend accounting or validation or inventory system may, for example, produce tamper-proof time and date stamps, logically associated with inventory as evidence of counts of instruments 108 and supplies 110, for instance at the start and at the end of a medical or clinical procedure.

The patient support structure 102 may take the form of a table (e.g., operating table), bed or other structure that may include a patient support surface 102a and a pedestal or base 102b that supports the patient support surface 102a. The patient support surface 102a should have dimensions sufficient to support at least a portion of a patient (not shown) during a medical or clinical procedure, for instance during surgery. Hence, the patient support surface 102a may have a length of six feet or more and a width of two feet or more. The patient support surface 102a may have two or more articulated sections (not shown), or may be an unarticulated or unitary structure as illustrated. Hinges or other coupling structures may couple any articulated sections. For instance, hinges may be located along a longitudinal axis of the patient support surface 102a at locations that would approximate the anticipated position of between a patient's legs and torso and between the patient's torso and head.

The patient support surface 102a is preferably made of a rigid material and is preferably radiolucent, allowing radiological imaging (e.g., X-rays, CAT scans, MRIs). Various radiolucent materials may be employed, for instance carbon fiber or radiolucent plastics (e.g., resin impregnated carbon fiber). Such advantageously allows radiological technologies to be employed, for example X-ray imaging. For example, the patient support surface 102a may be molded from plastics such as an acrylic or a phenolic resin (e.g., commercially available under the trademark SPAULDITE®). In some embodiments, the patient support structure 102 may include a frame. The frame may be made of a metal which may not be radiolucent. In such embodiments, the frame preferably makes up a small percentage of the total area of the patient support surface 102a. The patient support surface 102a may be capable of withstanding multiple cycles of sterilization (e.g., chemical, heat, radiation, etc.). A large variety of surgical tables, patient beds and other structures capable of supporting or carrying a patient or a portion of a patient are commercially available. Many of these commercially available structures include electric motors and electronics. Typically, there is no or minimal regulation of non-ionizing electromagnetic radiation generated by such electric motors and electronics. Hence, many medical or clinical procedure environments 100 in which medical or clinical procedures are performed tend to be electromagnetically noisy environments.

The patient support structure 102 may include one or more film receiving receptacles (not shown). The film receiving receptacles may be spaced relatively below a patient support surface 102a of the patient support structure 102. The film receiving receptacles are sized, dimensioned and/or positioned to receive film, for example X-ray film. The film receiving receptacles may be sized and/or dimensioned to receive a film tray or other film holder (not illustrated) which holds the film. Along with the use of radiolucent materials, such advantageously allows a patient X-ray images or other radiological images of the patient to be produced, generated or made, while the patient is supported by the patient support structure 102. As used herein an in the claims, the term radiolucent means substantially transmissive to energy in the X-ray portion of the electromagnetic spectrum, that is passing sufficient X-ray energy to produce an X-ray image at standard power levels and standard conditions employed in conventional medical imaging.

The pedestal or base 102b may be fixed, or may be moveable. The pedestal or base may include one or more actuators (e.g., motors, pumps, hydraulics, etc.) and/or drive mechanisms (e.g., gears, mechanical couplings) or linkages (not shown) that allow a position and/or orientation of the patient support surface 102a to be adjusted. For example, the pedestal or base may telescope to allow the patient support surface 102a to be mechanically raised and lowered. Also for example, the pedestal or base may allow the patient support surface 102a to be mechanically tilted or rotated about an axis that is perpendicular to the patient support structure 102.

The patient support structure 102 may include one or more drapes, mattresses or pads 134, and/or may include one or more sheets (not illustrated). The drapes, mattresses or pads 134 may take a variety of forms, and may be disposable, or may be capable of withstanding multiple cycles of sterilization (e.g., chemical, heat, radiation, etc.). The drapes, mattresses or pads 134 are preferably radiolucent (e.g., interior of cotton or a foam material such as a closed or an open cell foam rubber or LATEX®, liquid or a gas, exterior of cotton, nylon, rayon or other natural or synthetic materials). The drapes, mattresses or pads 134 may take a conventional form, for example cotton, open cell or a closed cell foam rubber, with or without an appropriate cover. Alternatively, the drapes, mattresses or pads 134 may include one or more bladders (e.g., dual layer urethane envelope) to receive a fluid (e.g., air, water, etc.) to selectively inflate one or more portions of the mattresses or pads, and/or to control a temperature of one or more portions of the mattresses or pads. In such embodiments, the fluid should be radiolucent. The drapes, mattresses or pads 134 may be detachably secured to the patient support structure 102 via various fasteners, for instance ties, or hook and loop fastener commonly available under the trademark VELCRO®.

The tables or stands 104 may take a variety of forms. For instance, the tables or stands 104 may include one or more instrument tables, supply tables, Mayo stands or tables and/or back tables. The table(s) or stand(s) 104 may include a generally planar surface, which may be supported by legs, or supported by brackets attached to a fixed structure such as a wall. Some tables or stands 104 may include a recess or opening (not shown), for example to receive a bucket or tray. The table(s) or stand(s) 104 are typically made of a metal, for instance a stainless steel. One or more of the table(s) or stand(s) 104 may be movable, for example including wheels or coasters. One or more of the table(s) or stand(s) 104 may be fixed. A portion of one or more tables or stands 104 may extend over the patient support structure 102, and hence the patient, during use. Often the table or stand 104 will be covered by one or more sterile drapes or mats 136a. In addition to carrying instruments 108 and/or supplies 110, the tables or stands 104 may carry any other object including medical procedure related equipment, trays or totes 114, buckets, implants, etc.

One or more receptacle(s) 106a are preferably wirelessly shielded (e.g., Faraday cages), to prevent wireless (e.g., radio or microwave frequency) communications between an interior 137 of the receptacle 106a and an exterior 138 thereof, at least in a closed configuration. The one or more receptacle(s) 106a may receive medical instruments 108 or supplies 110, for example used sponges or gauze, and hence may be denominated as waste receptacles. In some implementations, the receptacle(s) 106a may receive unused instruments 108 or supplies 110, for example to allow interrogation in a shielded environment that is shielded from the various sources of noise present in many medical or clinical environments. The receptacle(s) 106a may take a variety of forms, for example buckets. Such receptacle(s) 106a may be open, or may have a cover, lid or door 139a that is selectively positionable between open (illustrated in FIG. 1) and closed positions or configurations. Such receptacle(s) 106a may have a variety of shapes and sizes, and may be made of any number of materials, including but not limited to metals and plastics. The receptacle(s) 106a may include a disposable liner. The receptacle(s) 106a may, for example, include wheels or coasters to allow easy movement thereof, or may omit such.

The RFID interrogation system(s) may, for example, include one or more room-based RFID interrogation system 120a that includes one or more RFID interrogators or readers 140 and one or more antennas 142a-142e (collectively 142) communicatively coupled to the RFID interrogator(s) or reader(s) 140. Commonly available RFID interrogators or readers 140 typically operate in high frequency range (e.g., 13.56 Hz), or ultra-high frequency range (e.g., 433 MHz, 860 MHz to 960 MHz). Antennas 142 may be spaced about the medical or clinical environment 100, providing complete or substantially complete (e.g., 85% or greater) coverage of unshielded portions of the medical or clinical environment 100.

Alternatively or additionally, the RFID interrogation system(s) may, for example, include one or more hand-held RFID interrogator 140d to interrogate instruments and/or supplies 110 on the first table or stand 104.

Figure 8:
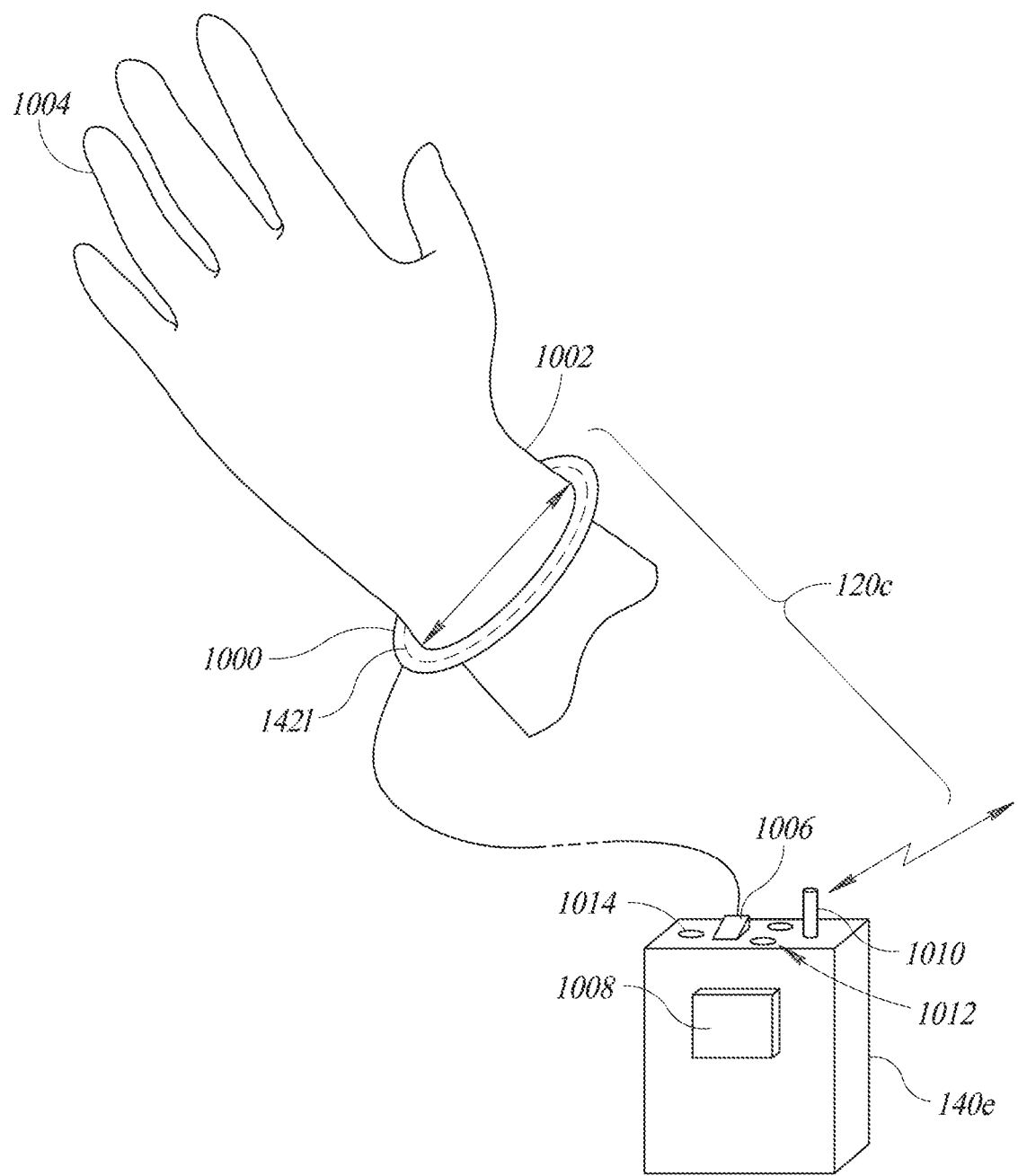
FIG. 8 is an isometric view of a body-worn antenna and interrogator or reader communicatively coupled to the antenna, according to at least one illustrated implementation.

Alternatively or additionally, the RFID interrogation system(s) may, for example, include one or more body-worn hand-held RFID interrogation system 120c including a body-worn interrogator or reader 140e and a body-worn antenna 142l, for instance as discussed in reference to FIG. 8 herein.

Alternatively or additionally, the RFID interrogation system(s) may, for example, include one or more drapes or mats 136a, which each include one or more antennas 142m communicatively coupled to an RFID interrogator or reader 140f.

The presence/absence interrogation system(s) 122 includes one or more presence/absence interrogators or readers 144 and one or more antennas 146a-146e communicatively coupled to the presence/absence interrogator(s) or reader(s) 144. The presence/absence interrogators or readers 144 may operate in the frequency range extending, for example, from about 137 kHz to about 160 kHz. Some of the antennas 146a-146d may be located in the drape, mattress or pad 134 used on the patient support surface 102a, providing complete or substantially complete coverage of a patient's body or sterile volume. One or more antennas 146e may be hand-held, for example incorporated as part of a wand 148. The handheld antenna 146e is communicatively coupled to the presence/absence interrogator(s) or reader(s) 144 by a wired or wireless communications path, for example via a coaxial cable or other communication path. The drape, mattress or pad 134 used on the patient support surface 102a may employ the structures and methods disclosed in U.S. Pat. No. 9,136,597. The presence/absence interrogation system(s) 122 may, for example, employ the structures and algorithms disclosed in U.S. Patent Application Publication No. 2011/0004276 and U.S. Patent Application Publication No. 2015/0272688.

The antennas 146 may take a variety of forms, for example coil antennas, dipole antennas, and/or slot antennas. Portions of one or more of the antennas 146 may overlap. For example, where the antennas 146 are coil antennas, each formed of one or more coils, a portion of an area enclosed by an outermost coil of each antenna may overlap a portion of an area enclosed by an outermost coil of a neighboring antenna. In such embodiments, neighboring antennas 146 may be electrically insulated from one another, for example by one or more electrically insulative layers or substrates. For example, successively adjacent antennas 146 may be carried on opposite surfaces (e.g., opposed outer surfaces, or multiple inner surfaces, or one or more outer and inner surfaces) of a single substrate. As discussed in more detail below, the antennas 146 may advantageously be radiolucent, for example being formed of a radiolucent material (e.g., substantially transparent to X-ray or Gamma ray radiation) or a material that at a thickness employed is substantially radiolucent. For example, an electrically conductive trace of aluminum having a thickness of 200 microns or less sufficiently passes X-rays to be considered radiolucent. More preferably, an aluminum trace having a thickness of 30 microns sufficiently passes X-rays such that even a stack or overlapping portions of three coils (combined thickness under 100 microns) may be radiolucent. An antenna may be considered radiolucent if it is not detectable by a radiologist in an X-ray produced via 10 kV to 120 kV X-ray machine, or preferably a 40 KV X-ray machine in conjunction with a standard 12 inch X-ray image intensifier. An antenna may be considered radiolucent if a coil includes thirty turns or windings and is not detectable by a radiologist in an X-ray.

In one implementation, personnel (e.g. counting nurse) can employ a hand-held RFID interrogator 140d to interrogate instruments and/or supplies 110 on the table or stand 104. The hand-held RFID interrogator 140d may be set to a "count in" or "scan in" mode or configuration, in which the hand-held RFID interrogator 140d identifies each unique identifier that is read as identifying an item being added to an inventory. The personnel (e.g. counting nurse) can employ the same hand-held RFID interrogator 140d to interrogate instruments and/or supplies 110 on the table or stand 104, or some other table or stand. For example, the personnel (e.g. counting nurse) can employ the hand-held RFID interrogator 140d to subsequently interrogate instruments and/or supplies 110 (e.g., used or discarded surgical sponges, gauze and/or padding 112c) on the table or stand 104. The hand-held RFID interrogator 140d may be set to a "count out" or "scan out" mode or configuration, in which the RFID interrogator 140d identifies each unique identifier that is read as identifying an item being removed from an inventory or otherwise being accounted for or having an accounted for status in the inventory. The hand-held RFID interrogator 140d may be set to a "count out" or "scan out" mode or configuration, in which the RFID interrogator 140d identifies each unique identifier that is read as identifying an item being removed or accounted for in the inventory. The hand-held RFID interrogator 140d may supply the information (e.g., unique identifier and count in or count out status) to the accounting system 130, for example via one or more wired or wireless communications channels.

In another implementation, personnel (e.g. counting nurse) can employ a body-worn hand-held RFID interrogation system 120c to interrogate instruments and/or supplies 110 on the table or stand 104.

As illustrated in FIG. 1 and better illustrated in FIG. 8, the body-worn hand-held RFID interrogation system 120c may include a body-worn antenna 1421, for example encased in a bracelet 1000 (FIG. 8) worn on a wrist 1002 or as encased in a ring worn on a finger 1004, and a body-worn interrogator or reader 140e. The body-worn interrogator or reader 140e may include a receptacle 1006 to detachably communicatively couple the body-worn antenna 1421 to the body-worn interrogator or reader 140e. The body-worn interrogator or reader 140e may, for example have a clip 1008 to allow the body-worn interrogator or reader 140e to be worn on a belt or vest. The body-worn interrogator or reader 140e may include an antenna 1010 to provide communications with the accounting system 130 (FIG. 1). The body-worn interrogator or reader 140e may include one or more visual indicators (e.g., LEDs, LCDs) 1012 and/or speakers 1014 for producing visual and aural alerts.

Returning to FIG. 1, the body-worn interrogator or reader 140e may be set to a "count in" or "scan in" mode or configuration, in which the body-worn interrogator or reader 140e identifies each unique identifier that is read as identifying an item being added to an inventory as the personnel sweeps the antenna over the first table 104. The personnel (e.g. counting nurse) can employ the same hand-held body-worn interrogator or reader 140e to interrogate instruments and/or supplies 110 on the table or stand 104 or some other table or stand. For example, the personnel (e.g. counting nurse) can employ the body-worn interrogator or reader 140e to subsequently interrogate instruments and/or supplies 110 (e.g., used or discarded surgical sponges, gauze and/or padding 112c) on the table or stand 104. The body-worn interrogator or reader 140e may be set to a "count out" or "scan out" mode or configuration, in which the body-worn interrogator or reader 140e identifies each unique identifier that is read as the personnel sweeps the antenna over the first table 104 as identifying an item being removed from an inventory or otherwise being accounted for or having an accounted for status in the inventory. The body-worn interrogator or reader 140e may be set to a "count out" or "scan out" mode or configuration, in which the body-worn interrogator or reader 140e identifies each unique identifier that is read as identifying an item being removed or accounted for in the inventory. The body-worn interrogator or reader 140e may supply the information (e.g., unique identifier and count in or count out status) to the accounting system 130, for example via one or more wired or wireless communications channels.

In a further implementation, the one or more tables or stands 104 may carry a respective drape or mat 136a, which each include one or more antennas 142m communicatively coupled to an RFID interrogator or reader 140f. A set of drape- or mat-based antennas 142m can interrogate instruments and/or supplies 110 on the table or stand 104. The RFID interrogator 140f may identify each unique identifier that is read via the set of drape- or mat-based antennas 142 as identifying an item being added to an inventory. The set of drape- or mat-based antennas 142m or another set of drape- or mat-based antennas can interrogate instruments and/or supplies 110 on the table or stand 104, or on some other table or stand. The RFID interrogator 140f may identify each unique identifier that is read via the second set of drape- or mat-based antennas 142m as identifying an item being removed from or accounted for in the inventory. The RFID interrogator 140f may supply the information (e.g., unique identifier and count in or count out status) to the accounting system 130, for example via one or more wired or wireless communications channels.

In some implementations can use a single drape or mat 136a, for example using the first table or stand 104 to initially count or scan in, and subsequently using the first table or stand 104 to count or scan out the instruments 108 and/or supplies 110. In such implementations, the interrogator or reader 140f may be manually switched between a "count in" or "scan in" mode or configuration and a "count out" or "scan out" mode or configuration. The RFID interrogator 140f may supply the information (e.g., unique identifier and count in or count out status) to the accounting system 130, for example via one or more wired or wireless communications channels. In other implementations, separate tables or stands and respective drapes or mats can be employed for count in and count out, respectively.

In a yet a further implementation, the patient support surface 102a of the patient support structure 102 may carry one or more drapes or mats 134, which each include one or more antennas 142o communicatively coupled to an RFID interrogator or reader 140f. A set(s) of drape- or mat-based antennas 142o can interrogate instruments and/or supplies 110 on the patient support surface 102a of the patient support structure 102. In such an implementation, the interrogator or reader 140f may be manually switched between a "count in" or "scan in" mode or configuration and a "count out" or "scan out" mode or configuration. The RFID interrogator 140f may supply the information (e.g., unique identifier and count in or count out status) to the accounting system 130, for example via one or more wired or wireless communications channels.

Figure 2A:
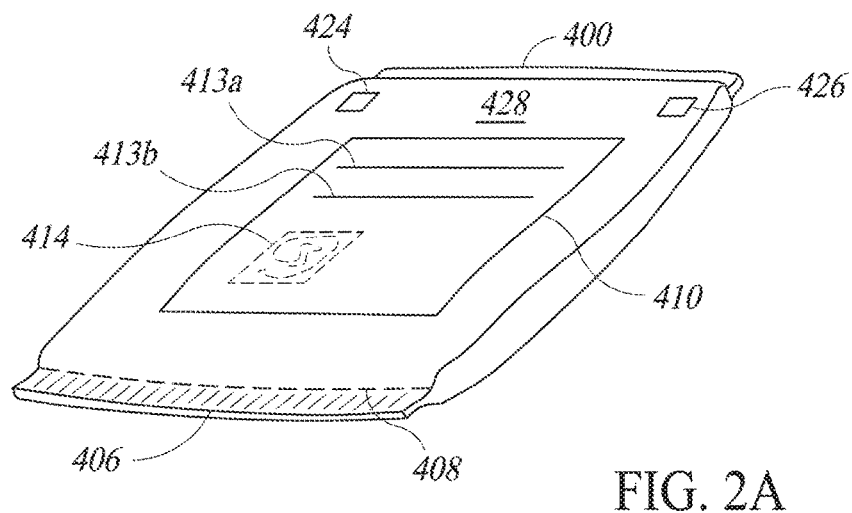
Figure 2B:
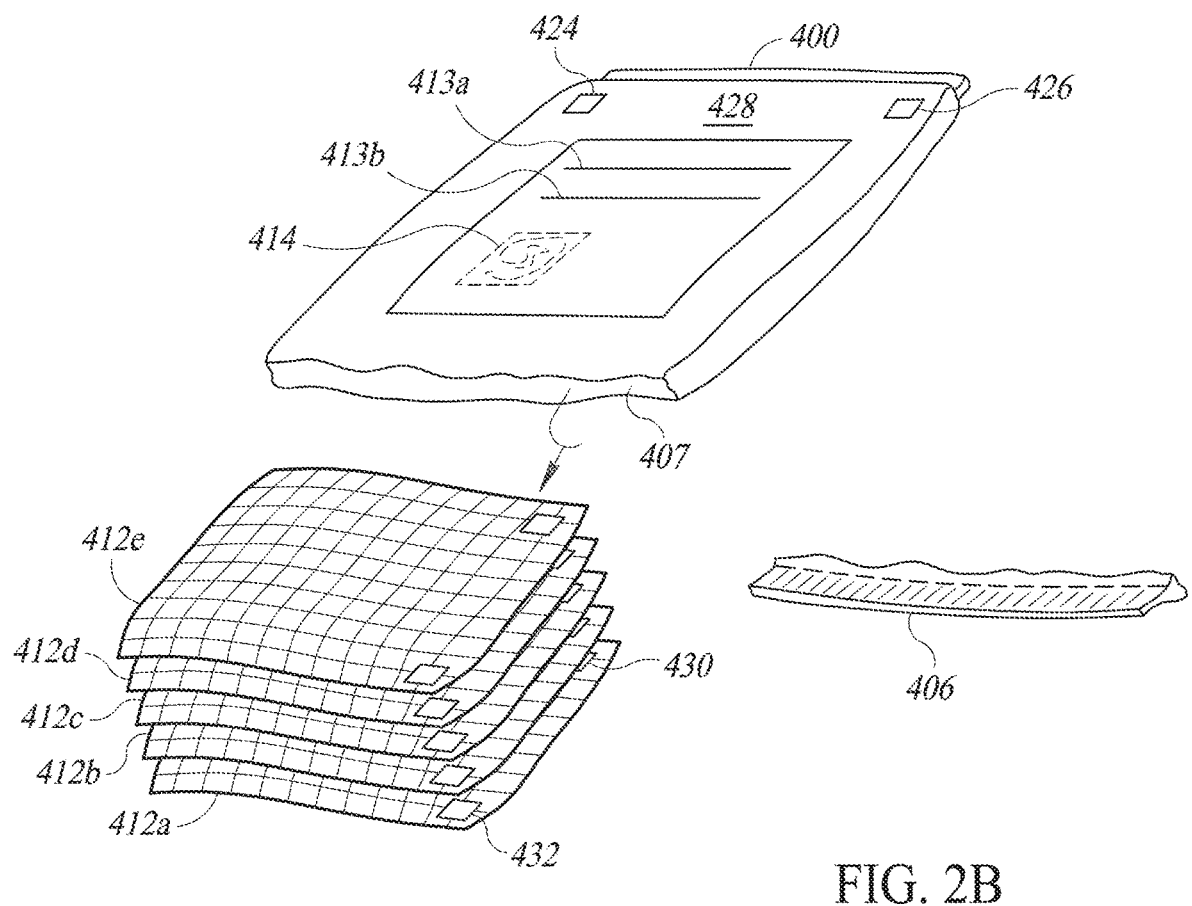
Figure 2C:
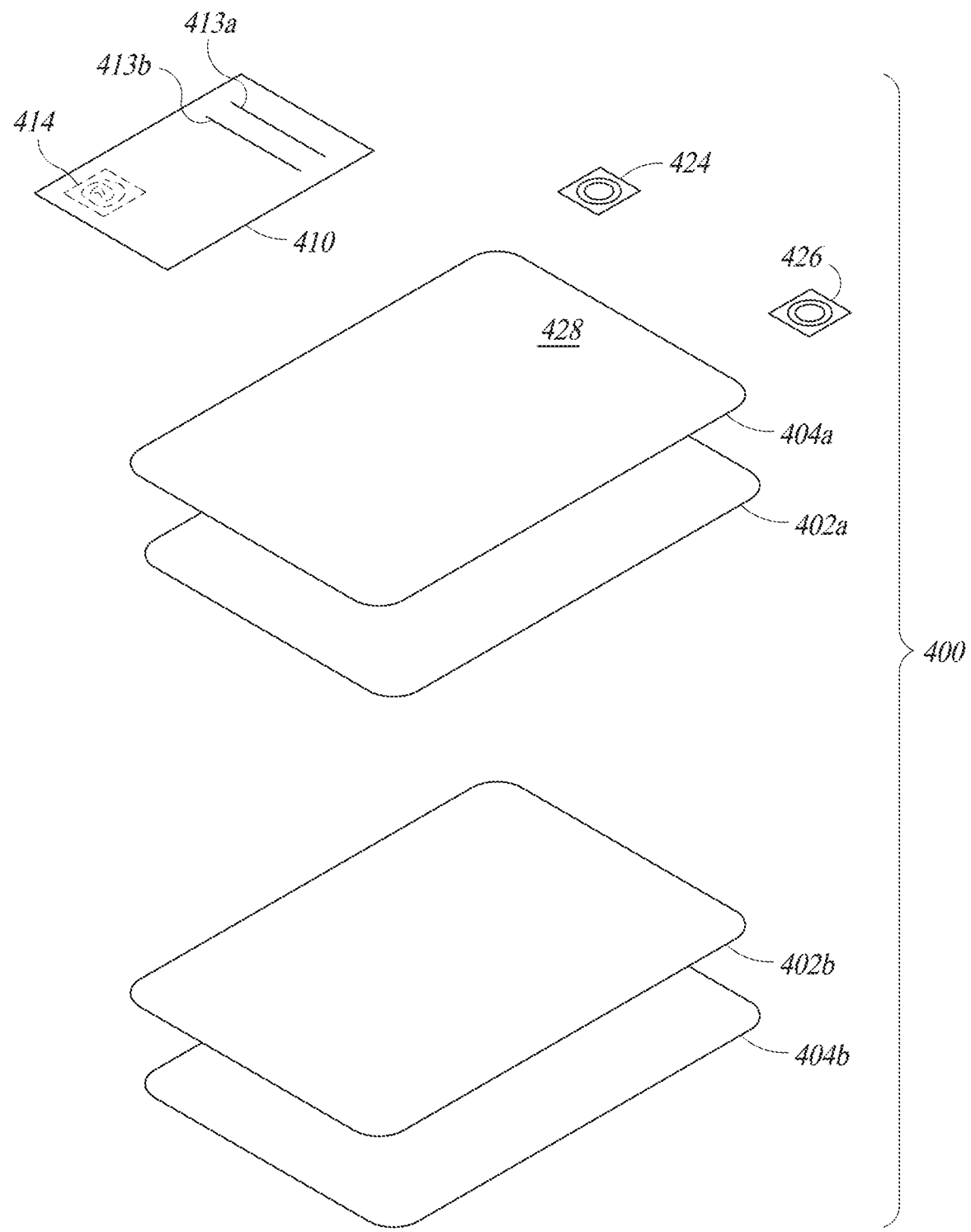
Figure 2D:
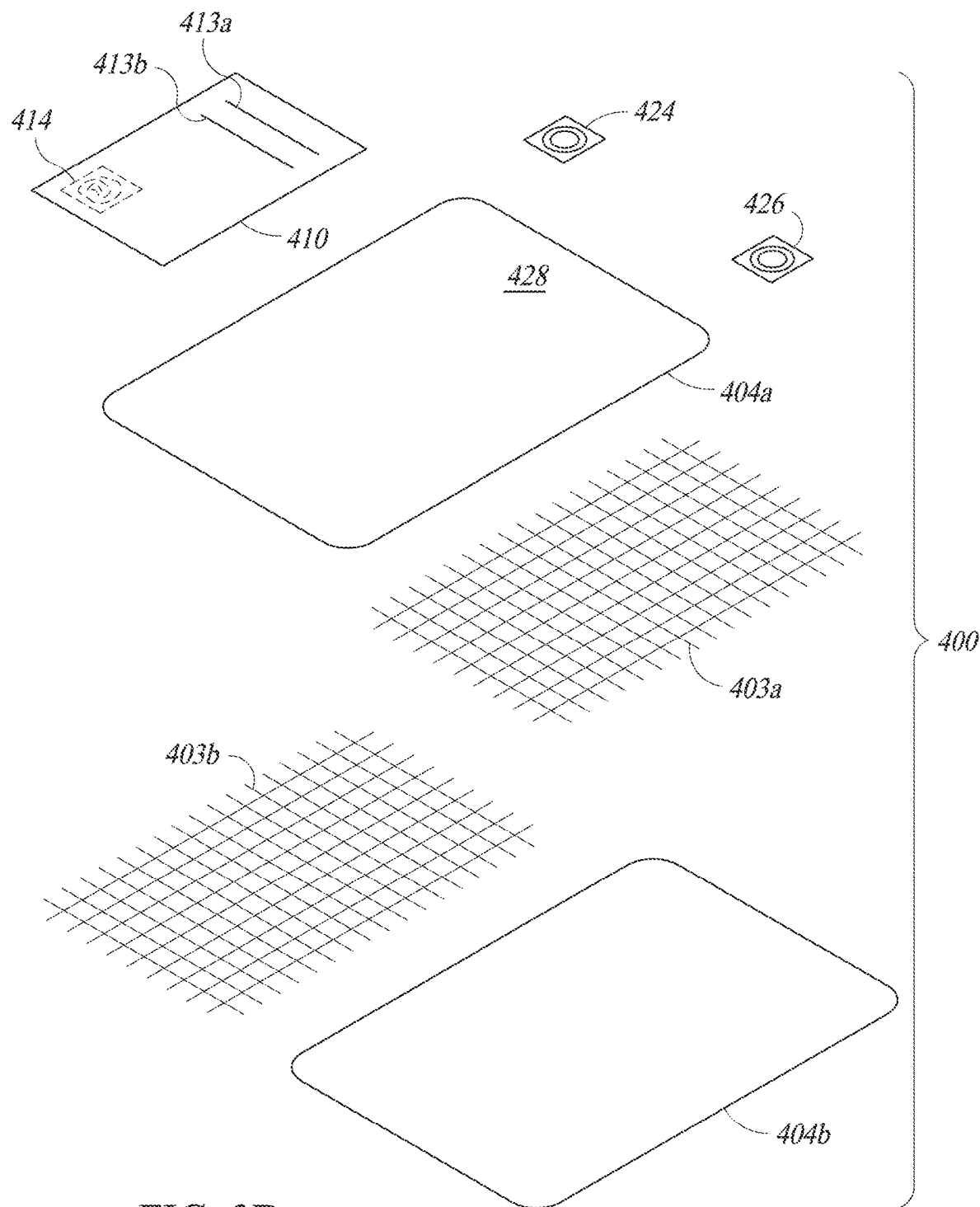

FIG. 2A shows a piece of shielded packaging 400 in a sealed or closed configuration, according to at least one illustrated implementation. FIG. 2B shows the piece of shielded packaging 400 in an unsealed or opened configuration, with the contents of the shielded packaging 400, in the form of surgical sponges, gauze and/or padding 412a-412e (collectively 412, five shown in FIG. 2B), removed from the piece of shielded packaging 400. FIG. 2C shows an exploded view of one implementation of the piece of shielded packaging 400. FIG. 2D shows an exploded view of another implementation of the piece of shielded packaging 400.

The piece of shielded packaging 400 can, as illustrated, take the form of, for example, a packet, envelope or sleeve. The piece of shielded packaging 400 can, for example, take the form of an electrically conductive foil packet, envelope or sleeve that serves as a shield (e.g., Faraday cage) to communications (e.g., radio frequencies, microwave frequencies) for the contents of the shielded packaging 400. The piece of shielded packaging 400 can, for example, comprise aluminum foil, copper foil, or a metalized substrate, for instance a metalized Mylar®, heat-sealable metalized paper polyethylene, heat-sealable metalized plastic laminate, etc. For example, as illustrated in FIG. 2C, the piece of shielded packaging 400 can include a pair of electrically conductive foil layers 402a, 402b laminated to respective non-electrically conductive outer packaging layers 404a, 404b. Alternatively, the shielded packaging 400 may comprise an electrically conductive mesh or grid, which may be laminated to, or sandwiched between electrically non-conductive materials 404a, 404b (e.g., Mylar®, plastic laminate, paper polyethylene, paper). For example, as illustrated in FIG. 2D, the piece of shielded packaging 400 can include a pair of electrically conductive mesh or grid layers 403a, 403b laminated to respective non-electrically conductive outer packaging layers 404a, 404b.

The piece of shielded packaging 400 can, for example, be closed via an adhesive or heat sealed 406 along at least one edge. The contents can advantageously be loaded into and sealed in an interior 407 (FIG. 2B) of the piece of shielded packaging 400 in a sterile environment. The piece of shielded packaging 400 may include a slit, notch or tear line 408, that facilitates opening, for example by tearing.

The piece of shielded packaging 400 may bear labeling 410. The label 410 can, for example, include one or more human-readable pieces of information 413a, 413b (e.g., alpha-numeric text or legends). The label 410 can, for example, include one or more optically machine-readable pieces of information, for example one or more machine-readable symbols 414 (e.g., one-dimensional or barcode symbols, two-dimensional or matrix code symbols). The information in the human-readable pieces of information 413a, 413b and/or encoded in the machine-readable symbol(s) 414 can identify the contents of the piece of shielded packaging 400 by name, quantity, manufacturer, and lot and/or batch number.

The piece of shielded packaging 400 may bear one or more wireless communications transponders, for example an RFID transponder 424 and/or a dumb wireless transponder 426. The RFID transponder and/or dumb wireless transponders 424, 426 are preferably located on an exterior 428 of the piece of shielded packaging 400 or at least exterior to a shield layer of the piece of shielded packaging 400. The RFID transponder and/or dumb wireless transponders 424, 426 can be retained via an adhesive or can be heat welded or RF welded to the piece of shielded packaging 400. The RFID transponders 424 can store and return information that identifies the contents of the piece of shielded packaging 400 by name or description (e.g., 4×4 gauze), quantity (e.g., 10 pieces), manufacturer, lot and/or batch number, date of manufacture and/or expiration date.

The contents, for example absorbent surgical sponges, gauze and/or padding 412, may bear one or more wireless communications transponders, for example an RFID transponder 430 (only one called out in FIG. 2B) and/or a dumb wireless transponder 432 (only one called out in FIG. 2B). The RFID transponder and/or dumb wireless transponders 430, 432 can be attached to an exterior surface or an inner surface (e.g., interior folded surface) of the surgical sponges, gauze and/or padding 412. The RFID transponder and/or dumb wireless transponders 430, 432 can be retained via an adhesive, can be heat welded or RF welded to the surgical sponges, gauze and/or padding 412, stitched thereto by cotton or other natural or synthetic thread or fiber, and/or clamped thereto via one or more fasteners (clamp, rivet, snap, staple). The structures and techniques disclosed in U.S. Patent Application Publication No. 2014/0303580, U.S. patent application Ser. No. 15/003,524, and U.S. patent application Ser. No. 15/053,956 may be employed to secure the RFID transponder and/or dumb wireless transponders 424 to the surgical sponges, gauze and/or padding 412. The RFID transponders 430 can store and return information that identifies the contents of the piece of shielded packaging 400 by name, quantity, manufacturer, lot and/or batch number, date of manufacture and/or expiration date.

Figure 3A:
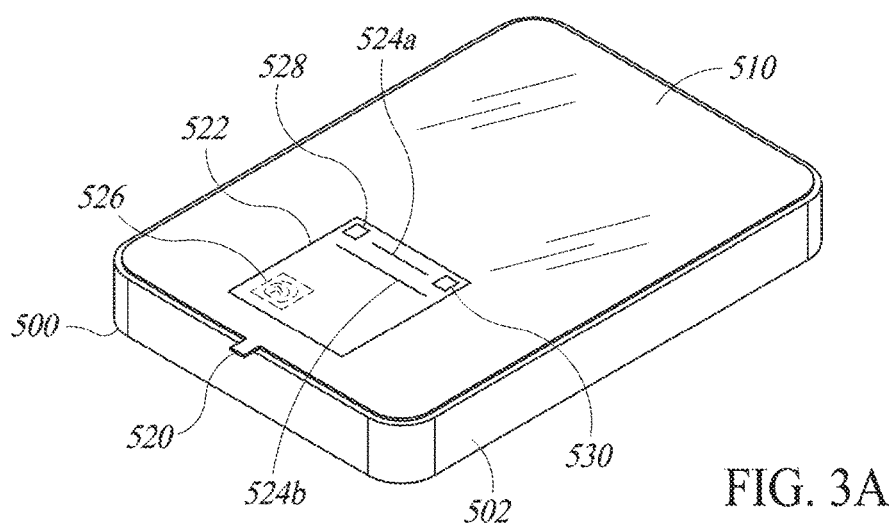
Figure 3B:
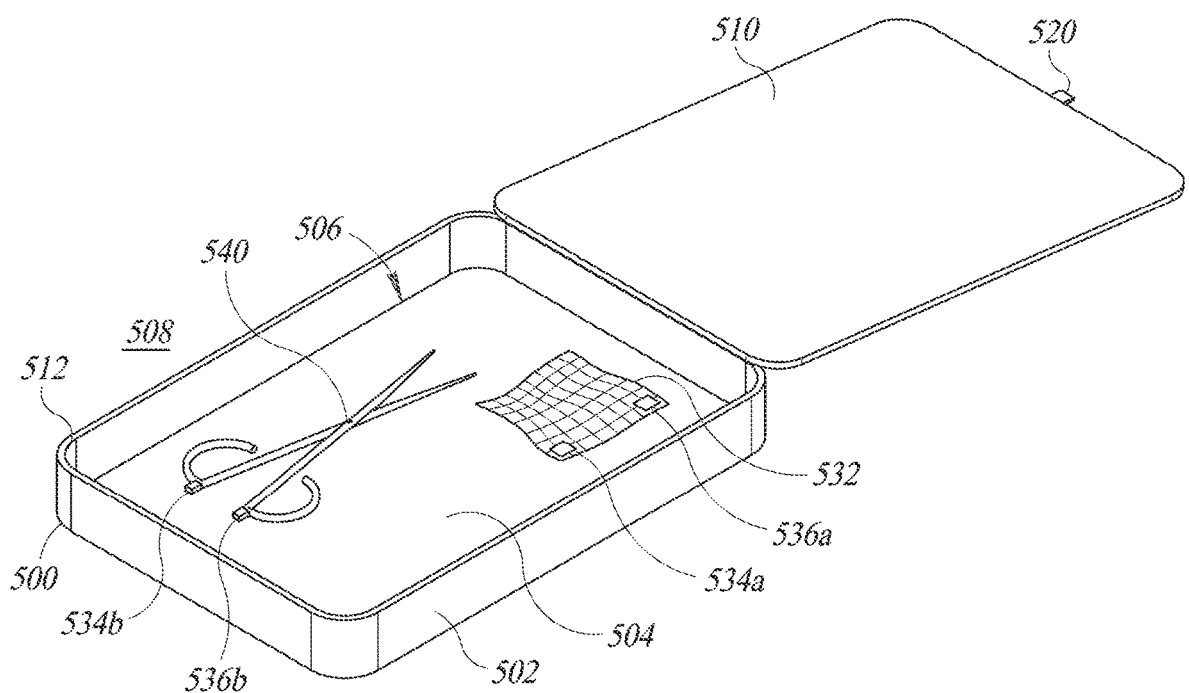
Figure 4A:
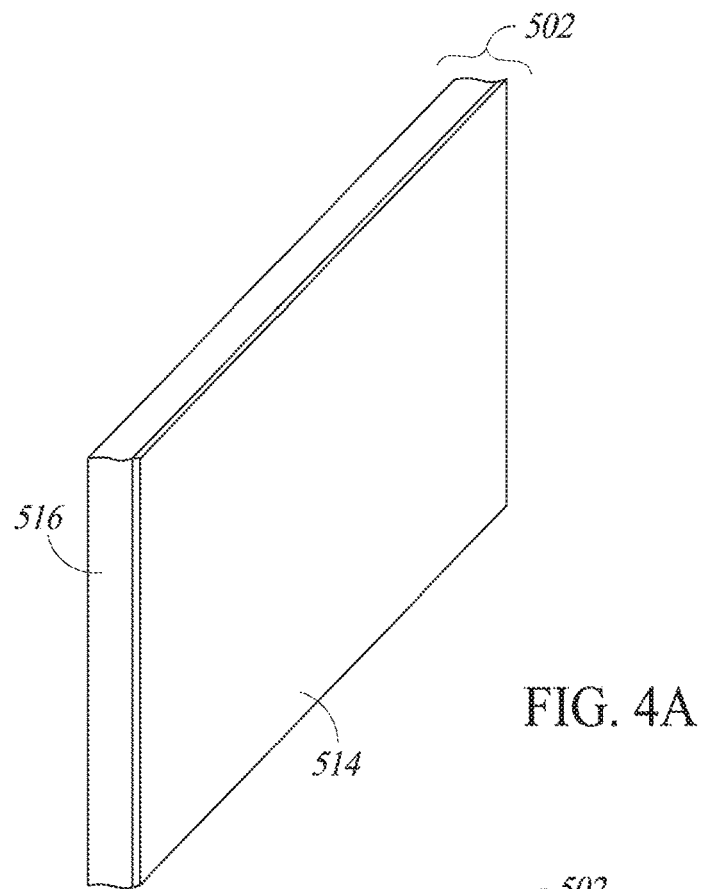
FIG. 4A is an isometric view of a portion of the shielded tote or shielded tray of FIGS. 3A and 3B, which, according to at least one illustrated implementation, can include a packaging layer and a foil shield layer.
Figure 4B:
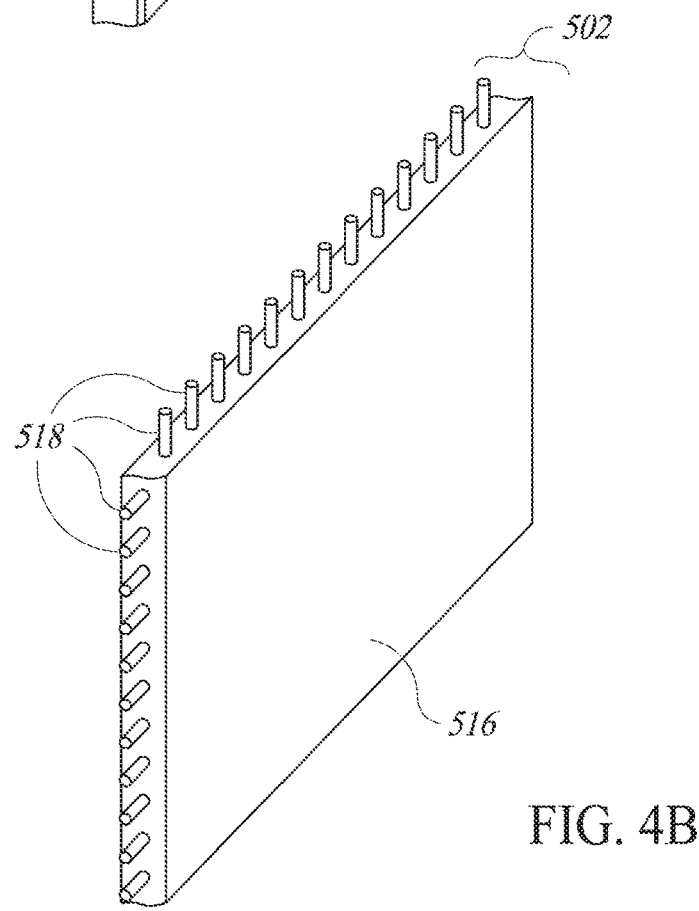
FIG. 4B is an isometric view of a portion of the shielded tote or shielded tray of FIGS. 3A and 3B, which, according to at least one illustrated implementation can include a packaging layer and a grid shield layer.

FIG. 3A shows a shielded tote or tray 500 in a sealed or closed configuration, according to at least one illustrated implementation. FIG. 3B shows the shielded tote or tray 500 in an unsealed or opened configuration, according to at least one illustrated implementation. FIG. 4A shows a cross-section portion of a shielded tote or tray 500 according to one illustrated embodiment. FIG. 4B shows a cross-section portion of a shielded tote or tray 500 according to another illustrated embodiment.

The shielded tote or tray 500 includes body 502 that defines an interior 504 (FIG. 3A) and an opening 506 to selectively provide access to the interior 504 from an exterior 508 of the shielded tote or tray 500. The shielded tote or tray 500 includes a selectively releasable or removable lid or cover 510, which is movable from a sealed or closed configuration (FIG. 3A) to an unsealed or open configuration (FIG. 3B). The lid or cover 510 can, for example, be releasable retained along a lip 512 (FIG. 3B) of the body 502 that surrounds the opening 506, for instance via a pressure sensitive adhesive.

As illustrated in FIGS. 3A and 3B, the body 502 may be formed of an electrically conductive material, for example a metal, for instance stainless steel. The lid or cover 510 can be formed of an electrically conductive material, for example a metal, for instance stainless steel, or more preferably a metal foil (e.g. aluminum foil, copper foil), or a metalized flexible substrate, for instance a metalized Mylar®, metalized paper polyethylene, metalized plastic laminate, cardboard, fiberboard, etc. The combination of the body 502 and the lid or cover 510 shield (e.g., Faraday cage) the contents of the shielded tote or tray 500 when in the sealed or closed configuration. Removal of the lid or cover 510 exposes the contents of the shielded tote or tray 500 to interrogation signals and allows responses to be sent.

Alternatively, as illustrated in FIG. 4A, the body 502 of the shielded tote or tray 500 can for example include one or more electrically conductive foil layers 514 laminated to a respective non-electrically conductive outer packaging layer or substrate (e.g., plastic, cardboard, fiberboard) 516.

Alternatively, as illustrated in FIG. 4B, the body 502 of the shielded tote or tray 500 can for example include one or more electrically conductive mesh or grid layers 518 laminated to or encased in a respective non-electrically conductive outer packaging layer or substrate (e.g., plastic, cardboard, fiberboard) 516.

The shielded tote or tray 500 can, for example, be closed via an adhesive or heat sealed along at least one edge. The contents can advantageously be loaded into and sealed in the interior 504 (FIG. 3B) of the shielded tote or tray 500 in a sterile environment. Alternatively, the contents can be sterilized while in the tote or tray 500, for instance after being hermetically seal via exposure to Gamma radiation and/or heat. The shielded tote or tray 500 may include a pull-tab 520, that facilitates opening, for example by releasing the lid or cover from the body.

The shielded tote or tray 500 may bear labeling 522 (FIG. 3A). The label 522 can, for example, include one or more human-readable pieces of information 524a, 524b (e.g., alpha-numeric text or legends). The label 522 can, for example, include one or more optically machine-readable pieces of information, for example one or more machine-readable symbols 526 (e.g., one-dimensional or barcode symbols, two-dimensional or matrix code symbols). The information in the human-readable pieces of information 524a, 524b and/or encoded in the machine-readable symbol(s) 526 can identify the contents of the shielded tote or tray 500 by name, quantity, manufacturer, and lot and/or batch number.

The shielded tote or tray 500 may bear one or more wireless communications transponders, for example an RFID transponder 528 and/or a dumb wireless transponder 530. The RFID transponder and/or dumb wireless transponders 528, 530 are preferably located on an exterior 428 of the shielded tote or tray 500 or at least exterior to a shield layer of the piece of shielded packaging 400. The RFID transponder and/or dumb wireless transponders 528, 530 can be retained via an adhesive or can be heat welded or RF welded to the piece of shielded packaging 400. The RFID transponders 528 can store and return information that identifies the contents of the shielded tote or tray 500 by name or description (e.g., 4×4 gauze), quantity (e.g., 10 pieces), manufacturer, lot and/or batch number, date of manufacture and/or expiration date.

The contents, for example absorbent surgical sponges, gauze and/or padding 532, may bear one or more wireless communications transponders, for example an RFID transponder 534a (only one called out in FIG. 3B) and/or a dumb wireless transponder 536a (only one called out in FIG. 3B). The RFID transponder and/or dumb wireless transponders 534a, 536a can be attached to an exterior surface or an inner surface (e.g., interior folded surface) of the surgical sponges, gauze and/or padding 532. The RFID transponder and/or dumb wireless transponders 534a, 536a can be retained via an adhesive, can be heat welded or RF welded to the surgical sponges, gauze and/or padding 532, stitched thereto by cotton or other thread or fiber, and/or clamped thereto via one or more fasteners (clamp, rivet, snap, staple). The structures and techniques disclosed in U.S. Patent Application Publication No. 2014/0303580 may be employed to secure the RFID transponder 534a and/or dumb wireless transponders 536a to the surgical sponges, gauze and/or padding 532. The RFID transponders 534a can store and return information that identifies the contents of the shielded tote or tray 500 by name, quantity, manufacturer, lot and/or batch number, date of manufacture and/or expiration date.

The contents, for example instruments 540, may bear one or more wireless communications transponders, for example an RFID transponder 534b (only one called out in FIG. 3B) and/or a dumb wireless transponder 536b (only one called out in FIG. 3B). The RFID transponder and/or dumb wireless transponders 534b, 536b can be attached to an exterior surface or an inner surface (e.g., interior folded surface) of the instruments 540. The RFID transponder and/or dumb wireless transponders 534b, 536b can be retained via an adhesive, can be a weld to the instruments 540, stitched or tied thereto by thread or wire, and/or clamped thereto via one or more fasteners (clamp, rivet, snap, staple). The structures and techniques disclosed in U.S. Pat. Nos. 7,898,420 and 8,354,931 may be employed to secure the RFID transponder and/or dumb wireless transponders 534b, 536b to the instruments 540.

The RFID transponders 534a, 534b can store and return information that identifies the particular item (e.g., absorbent surgical sponges, gauze and/or padding 532, instrument 540) to which the RFID transponder 534a, 534b is attached. The information can, for example, include a name or description of the item (e.g., 4×4 gauze, forceps), manufacturer, lot and/or batch number, date of manufacture and/or expiration date.

The receptacle 106a may be formed of a conductive material, for example a sheet metal, for instance stainless steel. Alternatively other constructions are possible, for example as illustrated in FIGS. 5A and 5B.

Figure 5A:
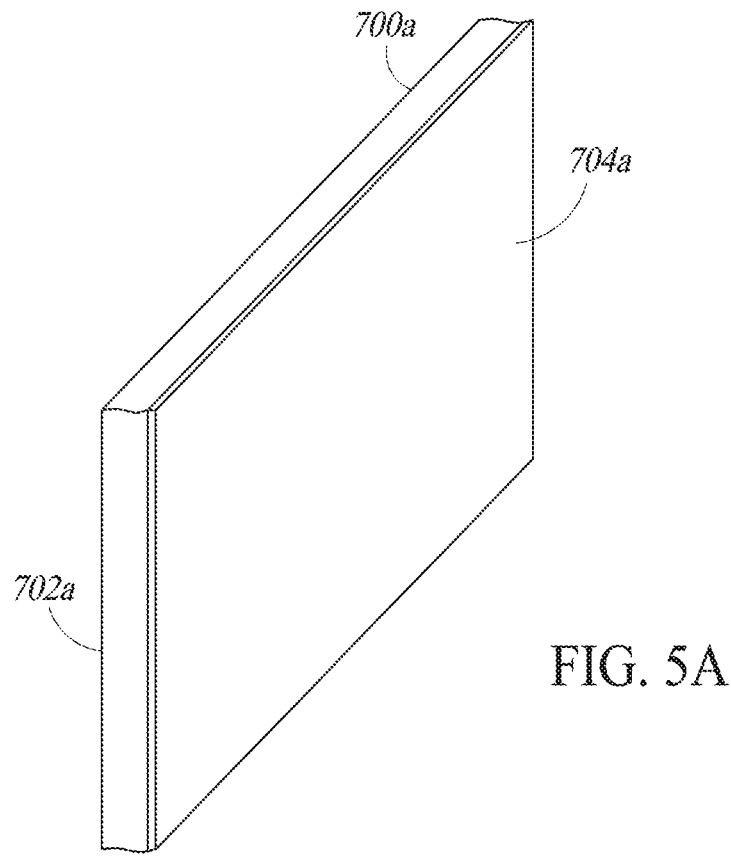
FIG. 5A is an isometric view of a portion of the shielded receptacle of FIG. 1, which, according to at least one illustrated implementation, can include a housing and a foil shield layer.

FIG. 5A shows a portion of a receptacle 700a, according to at least one illustrated implementation. The receptacle 700a may, for example, have a housing body 702a, which may be made of a non-conductive material (e.g., plastic) with a metal sheet or foil substrate 704a attached on an inner surface or an outer surface, or encased therein, and which forms a Faraday cage encompassing the interior of the receptacle 700a.

Figure 5B:
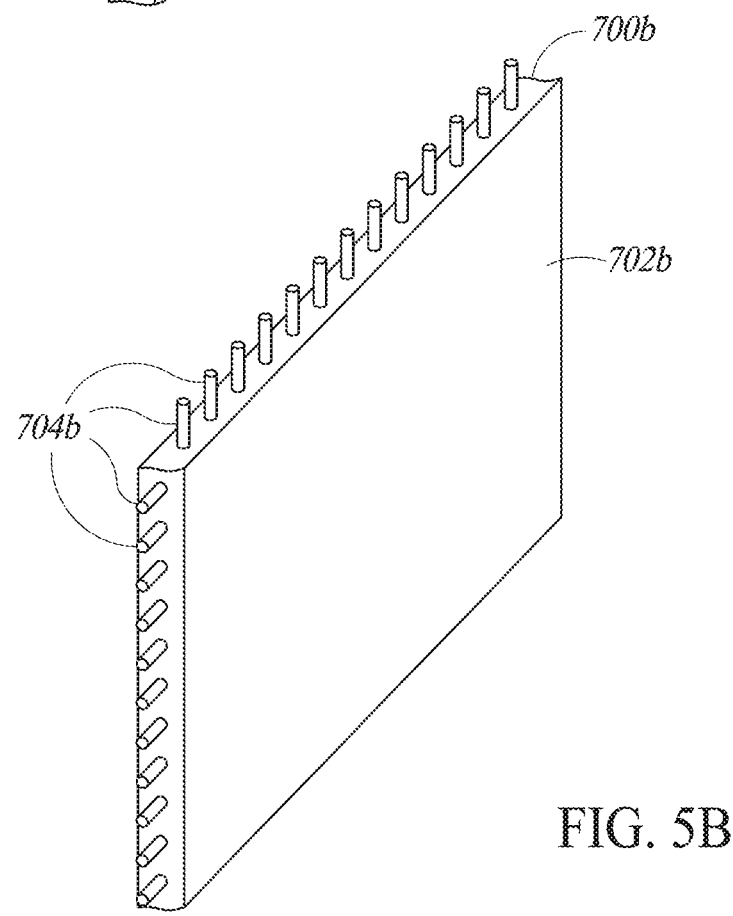
FIG. 5B is an isometric view of a portion of the shielded receptacle of FIG. 1, which, according to at least one illustrated implementation, can include a housing and a grid shield layer.

FIG. 5B shows a portion of a receptacle 700b, according to at least one illustrated implementation. The receptacle 700b may, for example, have a housing body 702b, which may be made of a non-conductive material (e.g., plastic), with a mesh or grid of metal wires or fibers 704b (four called out) attached encased therein or attached on an inner surface or an outer surface, and which form a Faraday cage encompassing the interior of the receptacle 700b.

Figure 6:
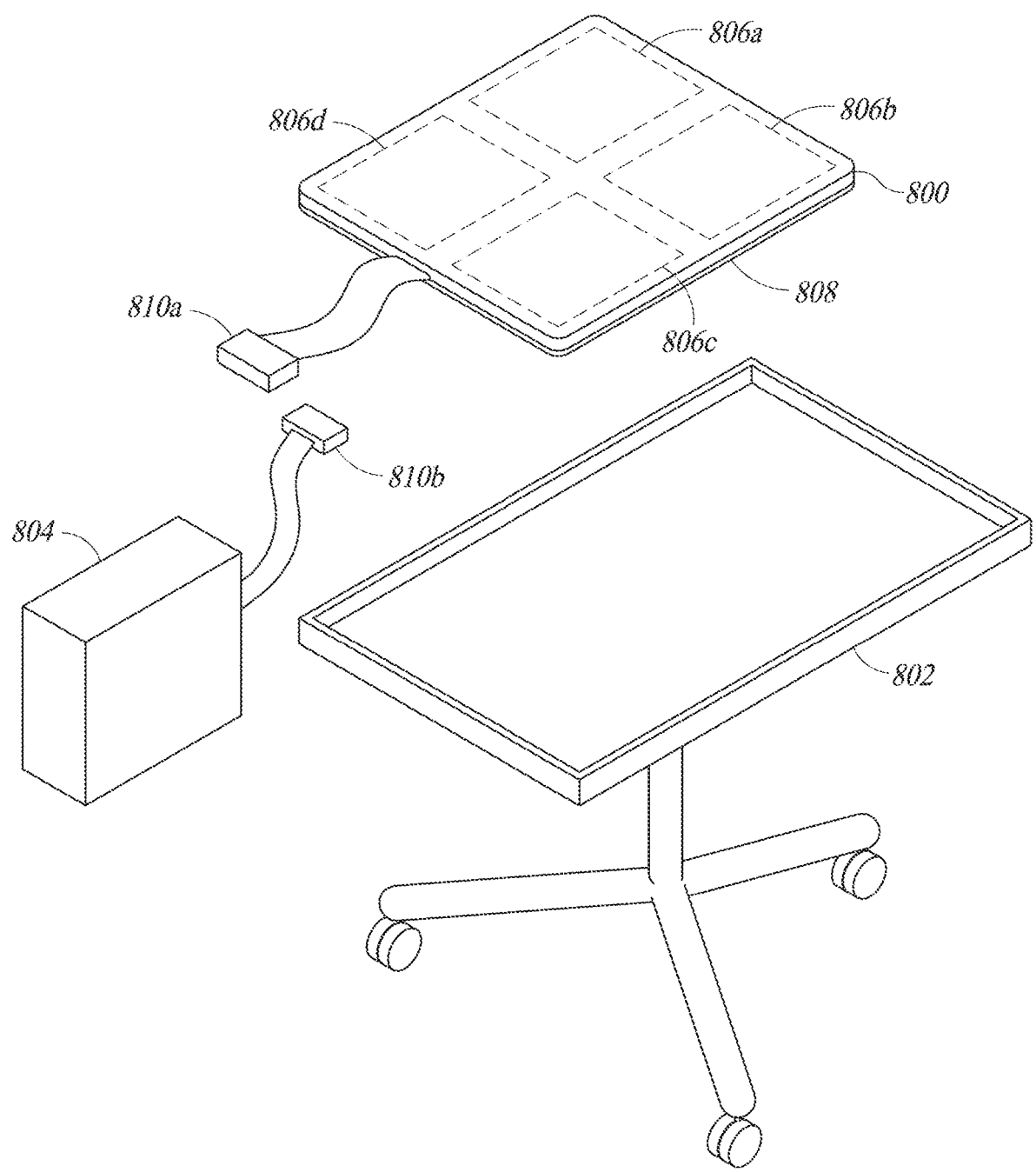
FIG. 6 is an isometric view of a pad or mat with one or more antennas according to one illustrated implementation, which can be used on a table or stand and communicatively coupled to an interrogator or reader to wirelessly read information from one or more wireless communications transponders attached to medical or clinical objects or items when carried on the table or stand.

FIG. 6 shows a mat 800, a table or stand 802 on which the mat 800 can be placed, and an RFID interrogator 804 that is communicatively coupleable to one or more antennas 806a-806d (four shown, collectively 806) physically coupled to or encased in the mat 800, according to at least one illustrated implementation.

The mat 800 houses or carries at least one antenna 806. Preferably, the antennas 806 are encased in the mat 800, which may be formed of an electrically non-conductive or electrically insulative material to prevent unintentional shorting of the antenna 806. One or more mats 800 may be positioned on or in the tables or stands 802 to position antennas 806 to interrogate items (e.g., instruments, supplies) carried on the mat 800. Additionally, one or more mats 800 may be located in or on a receptacle 106a, 106b (FIG. 1) to interrogate items (e.g., instruments, supplies) in the receptacle.

The mat 800 may take a variety of forms, and may be disposable, or may be capable of withstanding multiple cycles of sterilization (e.g., chemical, heat, radiation, etc.). The mat 800 or portions thereof may be electrically insulative. The mat 800 may be radiolucent, particular if the mat 800 is expected to be located between a patient and a radiological imaging source. The mat 800 may take a conventional form, for example cotton, open cell or a closed cell foam rubber, rubber or silicone, with or without a suitable cover. The mat 800 may optionally be detachably secured to the table or stand 802 via various fasteners, for instance ties, or hook and loop fastener commercially available under the trademark VELCRO®.

The antenna 806 may take a variety of forms, for instance a loop antenna, dipole antenna, slot antenna, etc. The antenna 806 may constitute an electrically conductive trace carried by the mat 800. For example, the antenna 806 may be carried on an outer surface of the mat 800 or carried in an interior of the mat 800, as illustrated in FIGS. 6 and 8. The antenna 806 may be radiolucent, for example being formed of a radiolucent material (e.g., substantially transparent to X-ray or Gamma ray radiation) or a material that at a thickness employed is substantially radiolucent. For example, an electrically conductive trace of aluminum having a thickness of 200 microns or less sufficiently passes X-rays to be considered radiolucent. More preferably, an aluminum trace having a thickness of 30 microns sufficiently passes X-rays such that even a stack or overlapping portions of three coils (combined thickness under 100 microns) may be radiolucent. An antenna may be considered radiolucent if it is not detectable by a radiologist in an X-ray produced via 10 kV to 120 kV X-ray machine, or preferably a 40 KV X-ray machine in conjunction with a standard 12 inch X-ray image intensifier. An antenna may be considered radiolucent if a coil includes thirty turns or windings and is not detectable by a radiologist in an X-ray.

The mat 800 may optionally include an RF shield 808. The RF shield 808 may take a variety of forms, which provide directional RF shielding. For instance, the RF shield 808 may comprise an electrically conductive plate or wire mesh to form a partial Faraday cage. Such may be used to ensure that only selected areas are interrogated. For example, such can be employed to ensure that only sterile fields associated with the tables or stands 102, 104 (FIG. 1) on which the mats 800 are located are interrogated. Such may advantageously be employed to ensure that transponders located in the body of the patient are not interrogated or read. The RF shield 808 may be generally planar, or may have one or more raised portions, for example an upstanding peripheral lip or edge (not shown).

Alternatively, the table or stand 802 or a portion thereof may consist of a metal such as a sheet of metal or mesh of metal wires, which functions as an RF or Faraday shield, and thus constitutes an RF shield to shield against radio and microwave frequencies. In particular, metal (e.g., stainless steel) may be on an outer surface of the table or stand 802, may be a layer in the table or stand 802 or may constitute the entire table or stand 802. Consequently, the mat 800 itself omits an RF shield.

A wired connector 810a may provide communicative coupling of the antenna 806 with a complementary wire connector 810b of the RFID interrogator or reader 804. The wire connecters 810a, 810b may have a standard interface (e.g., USB connectors) to allow selective coupling and uncoupling to the RFID interrogator or reader 804 via one of the ports thereof. Appropriate instructions (e.g., software, firmware) may be loaded in response to the coupling of the antenna 806 to the RFID interrogator or reader 804. For example, instructions may be loaded to a control subsystem of the RFID interrogator or reader 804.

The RFID interrogator or reader 804 can, for example, be an integral to the mat 800, hence denominated as an integral RFID interrogator or reader.

The RFID interrogator or reader 804 may take a variety of forms, but will typically include a transmitter and/or receiver, which may be formed as a transceiver. The transmitter and/or receiver are communicatively coupled to the antenna 806 by electrically conductive paths. The RFID interrogator or reader 804 may be configured to transmit interrogation signals and receive response signals. The RFID interrogator or reader 804 may further be configured to decode information encoded in the response signals, for example unique identifiers that uniquely identify the wireless identification or RFID transponders, which are emitted or backscattered as response signals to interrogation signals. Alternatively, the RFID interrogator or reader 804 may send the commands to the wireless identification or RFID transponders to control operation of the wireless identification or RFID transponders. For example, RFID interrogator or reader 804 may implement a singulation algorithm, to allow reading of a plurality of wireless identification or RFID transponders in a group. For instance, the RFID interrogator or reader 804 may send an interrogation signal, and cause each wireless identification or RFID transponder that is read to stop responding for a period of time, allowing the signals of other wireless identification or RFID transponders to be detected and decoded. Some wireless identification or RFID transponders are operable to set a random delay time before responding to an interrogation signal, facilitating singulation.

Figure 7A:
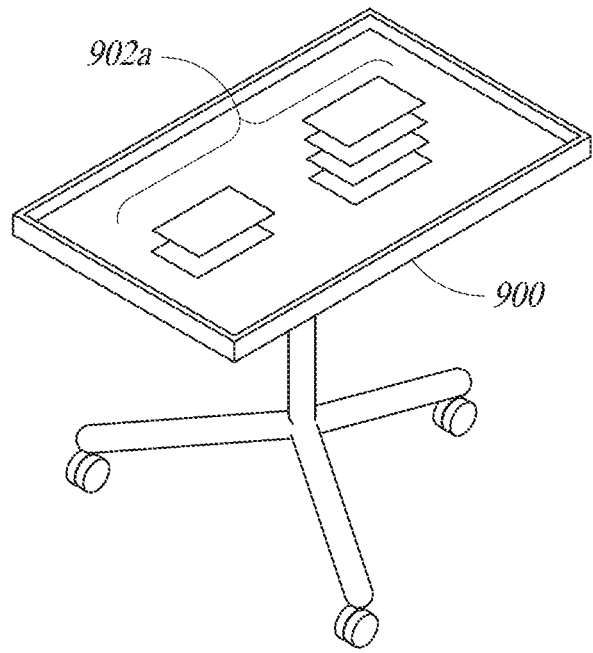
FIG. 7A is an isometric view of a pad or mat with one or more antennas, the pad or mat carried on a table or stand with a number of medical or clinical objects or items carried thereon, for example after or proximate an end of a medical or clinical procedure, according to at least one illustrated implementation.

FIG. 7A shows a first table or stand 900 with a number of supplies 902a for use in a medical or clinical procedure, according to at least one illustrated embodiment.

The first table or stand 900 may take any of a variety of forms, for example instrument tables, supply tables, Mayo stands or tables and/or back tables. Various supplies 902a are positioned on the first table, for example at or proximate a start of a medical or clinical procedure. Wireless identification or RFID transponders associated with the supplies are interrogated, and identifying information read and entered into a data store, for instance checked into an inventory database for the particular medical or clinical procedure. The wireless identification or RFID transponders may be interrogated using a handheld antenna, body-worn antenna, room antennas, or mat-based antenna.

Figure 7B:
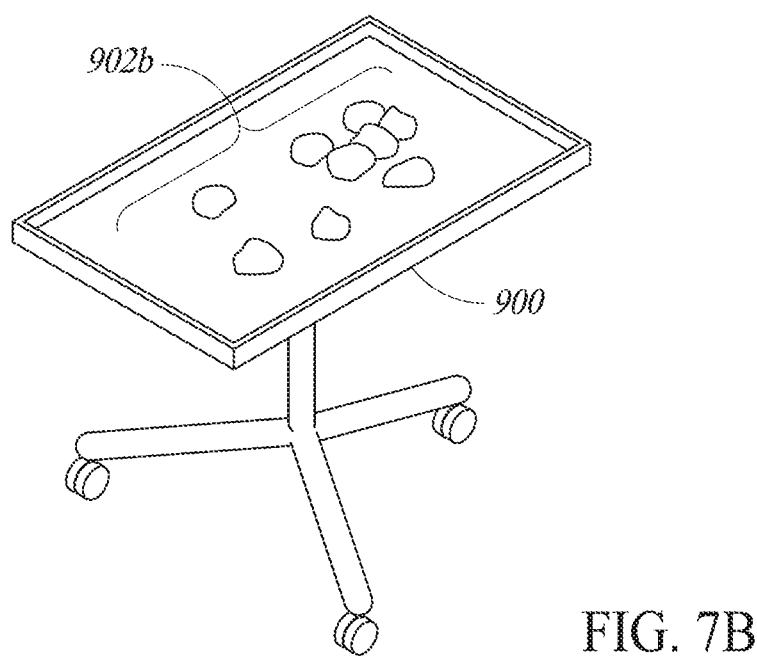
FIG. 7B is an isometric view of a pad or mat with one or more antennas, the pad or mat carried on a table or stand with a number of medical or clinical objects or items carried thereon, for example prior to or proximate a start of a medical or clinical procedure, according to at least one illustrated implementation.

FIG. 7B shows the first table or stand 900 with a number of supplies 902b which supplies have been used in a medical or clinical procedure, according to at least one illustrated embodiment.

Various used supplies 902b are positioned on the first table 900, for example at or proximate an end of a medical or clinical procedure. Wireless identification or RFID transponders associated with the supplies are interrogated, and identifying information read and entered into a data store, for instance checked out of an inventory database for the particular medical or clinical procedure. The wireless identification or RFID transponders may be interrogated using a handheld antenna, body-worn antenna, room antennas, or mat-based antenna. Notably, the same antenna and RFID interrogator can be used to interrogate the supplies on the first table or stand 900 at a first time (e.g., at or proximate a start of a medical or clinical procedure) and at a second time (e.g., at or proximate an end of a medical or clinical procedure).

Figure 9:
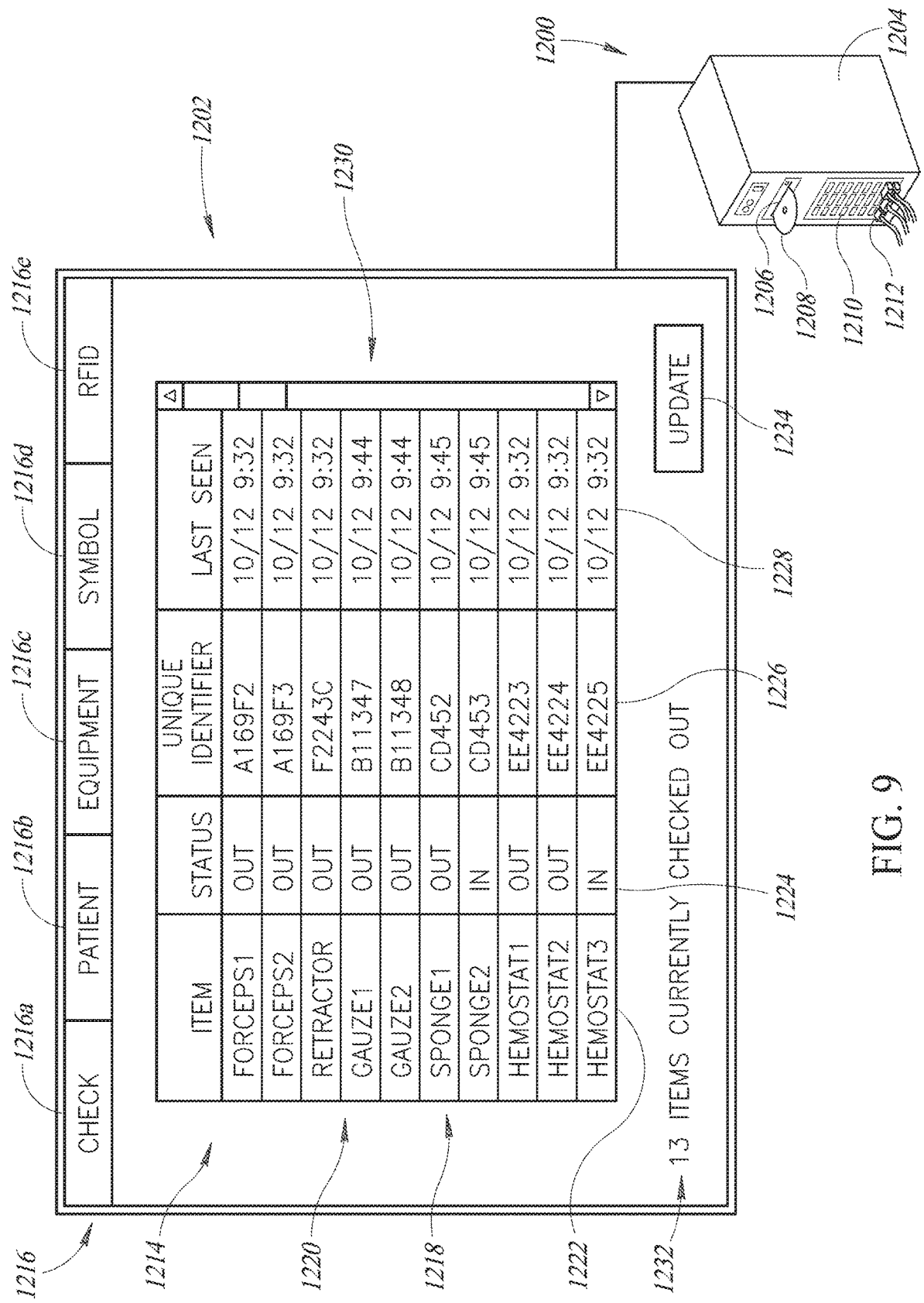
FIG. 9 is a front elevation view of an accounting system and display of the accounting system of FIG. 1, according to one illustrated embodiment.

FIG. 9 shows an accounting system 1200 and display 1202, according to one illustrated embodiment.

The accounting system 1200 may include a housing 1204 which houses one or more microprocessors, memory (e.g., RAM, ROM, FLASH), nontransitory computer- or processor-readable storage devices (e.g., hard disk drive, solid state drive), and buses (e.g., power bus, communications buses). The accounting system 1200 may include one or more slots 1206 or other receptacles to receive computer- or processor-readable media 1208, for instance spinning media (e.g., compact disks, DVDs), fixed media (e.g., Flash cards, secure digital (SD) cards, multimedia (MM) cards). The accounting system 1200 may also include one or more ports or connectors 1210 (only one called out in FIG. 9) to allow selective connection and disconnection of various devices to the control subsystem of the presence/absence interrogator or reader 1200. The connection may provide communications and/or power between the accounting system 1200 and various connected devices. Devices may take a variety of forms, for instance one or more radio frequency identification (RFID) interrogation systems 120a (FIG. 1), one or more wireless presence/absence interrogation systems 122 (FIG. 1), one or more computers or terminals 128 (FIG. 1), one or more antennas 142, 146 (FIG. 1), and any other device capable of transmitting or receiving data and/or instructions or capable of any other form of communications. Such ports or connectors 1210 may take the form of various industry standard ports or connectors, for example Universal Serial Bus ports. While illustrated as physical ports to couple with a connector or plug 1212 (only one called out in FIG. 9), the ports 1210 may take the form of one or more wireless transmitters, receivers or transceivers. Such may, for instance be compatible with various industry standards, for instance 802.11b, 802.11c, 802.11n, or BLUETOOTH®. Various interfaces may provide access to remote services, such as the Internet or "cloud" storage, or to other computing devices.

The display 1202 may be any screen or monitor suitable to display information and/or a user interface (e.g., graphical user interface). The display 1202 may, for example take the form of an LCD display panel or a CRT display. The display 1202 may be a standalone, separate piece of equipment. Alternatively, the display 1202 may be integrated into the housing 1204 of the accounting system 1200.

Figure 10:
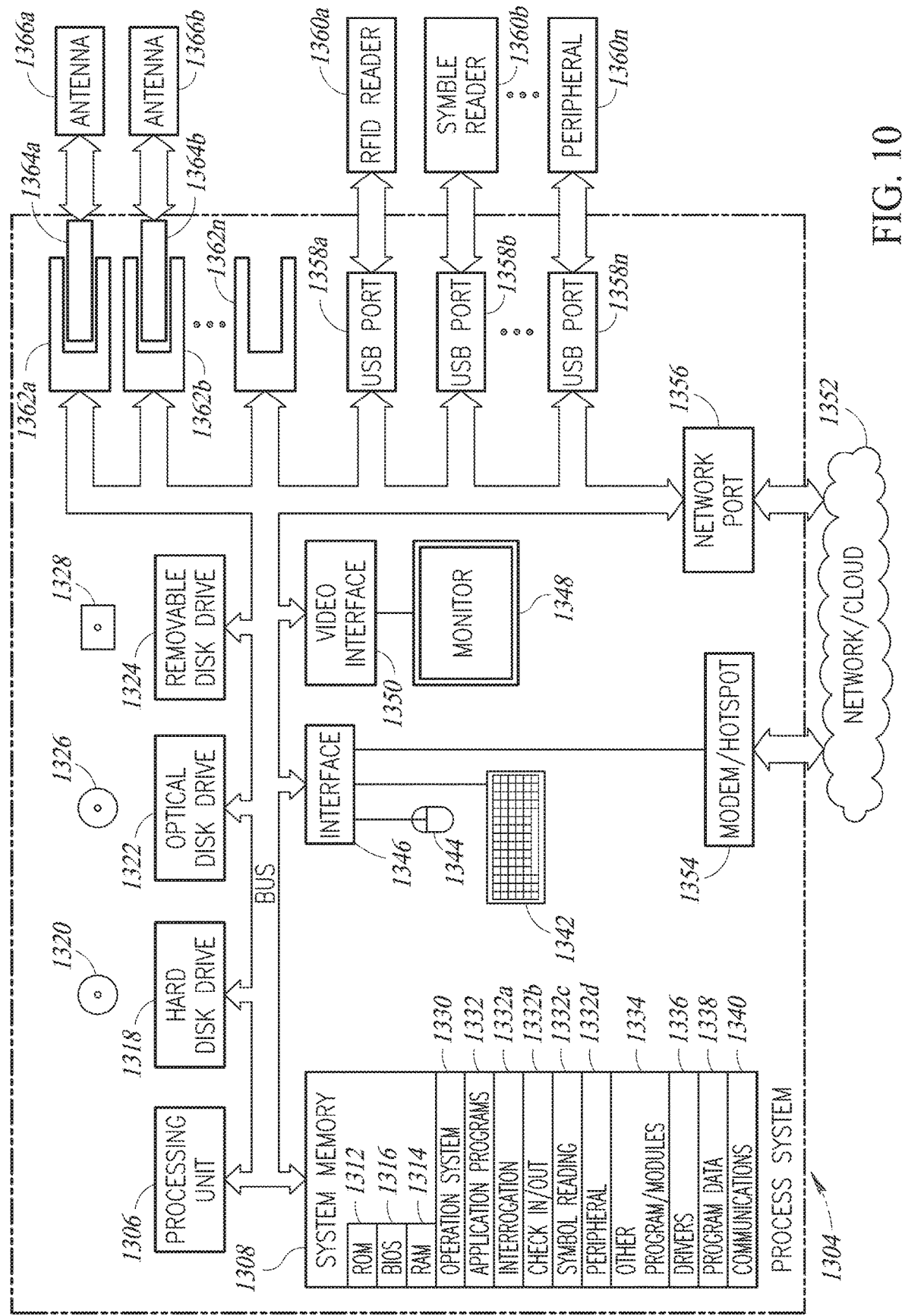
FIG. 10 is a schematic diagram of a control subsystem according to one illustrated embodiment, the control subsystem including a processor system, plug-in boards and various ports to provide communications with antennas, readers and various non-reader peripheral devices or equipment.
Figure 11A:
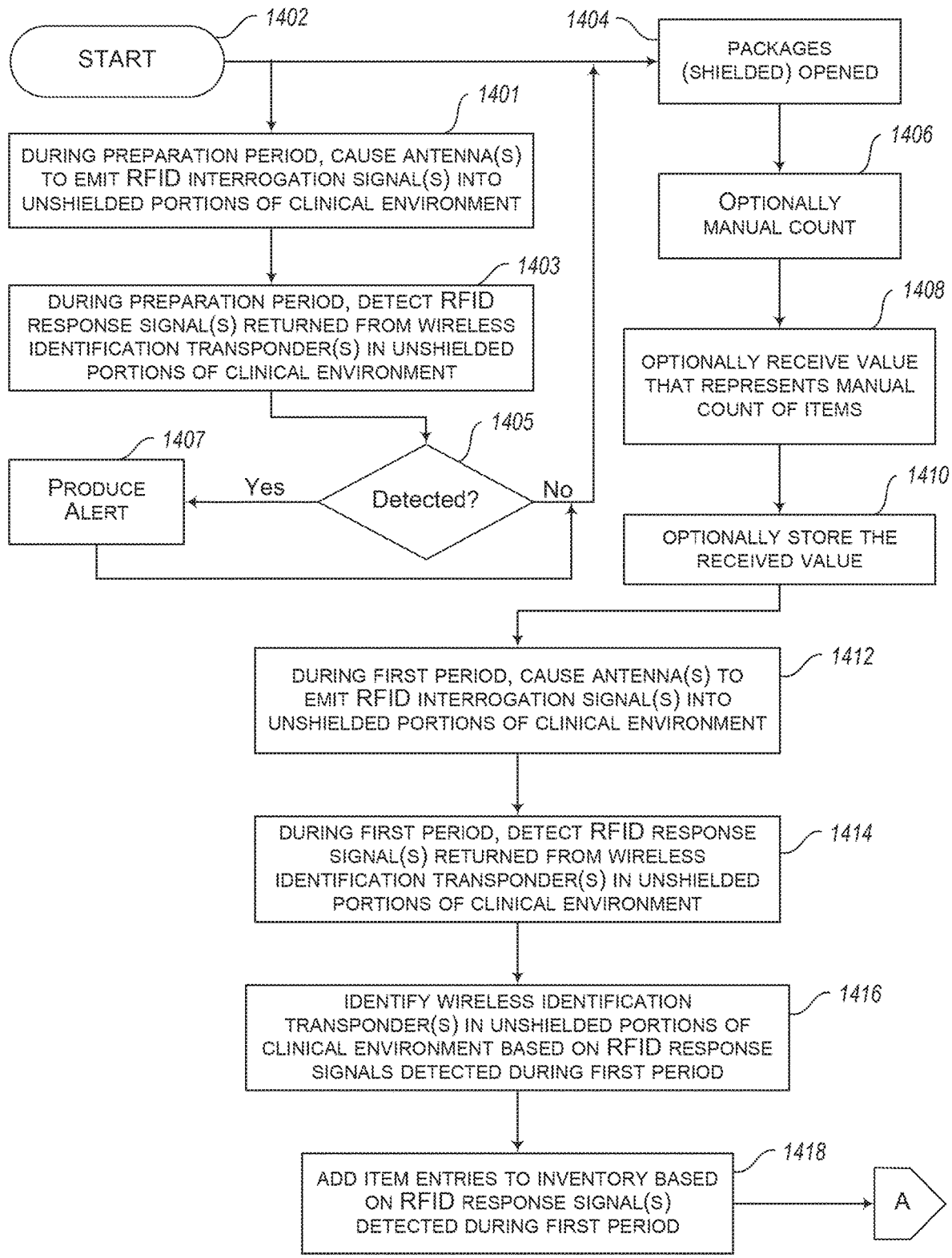
Figure 11B:
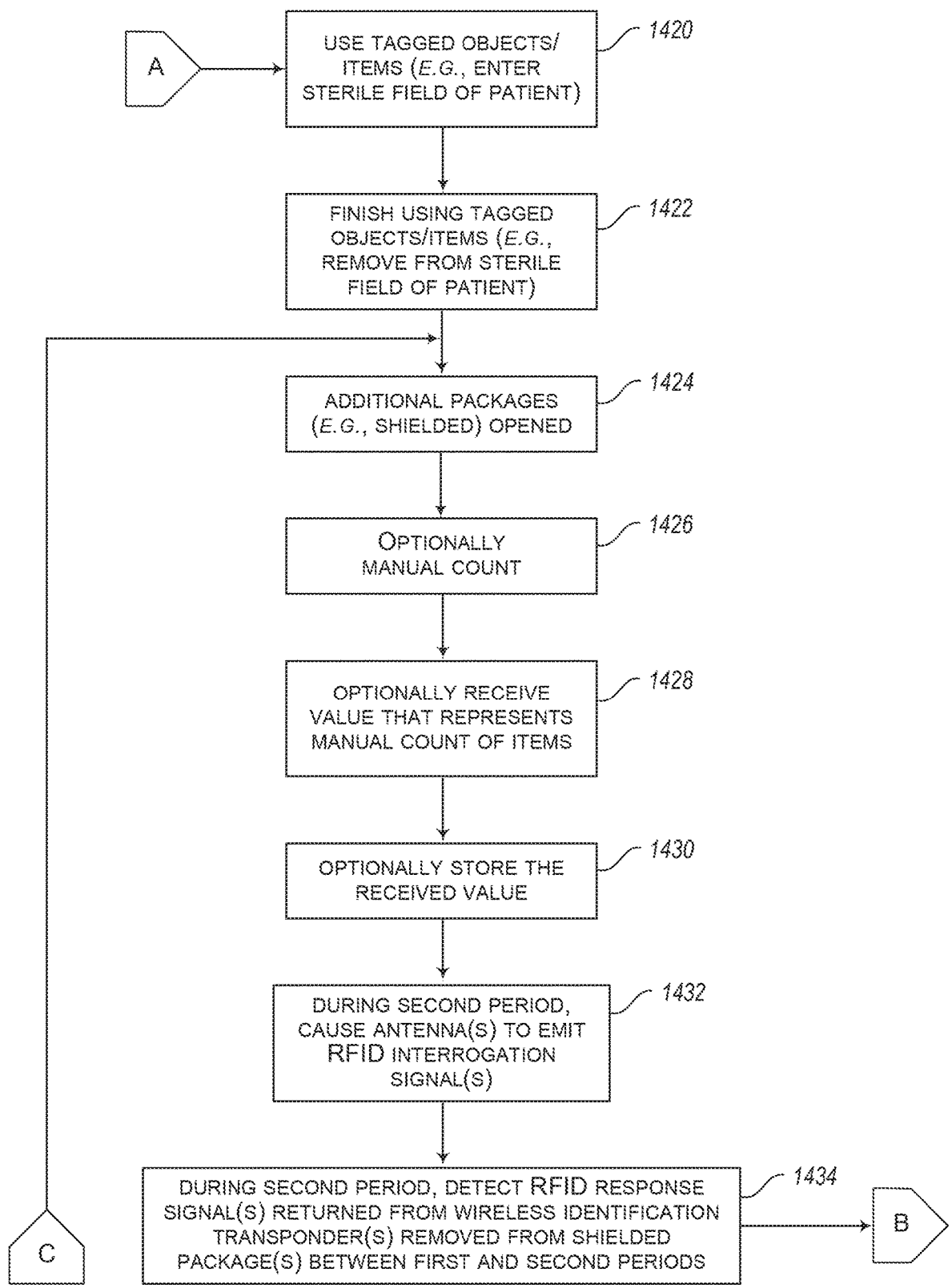
Figure 11C:
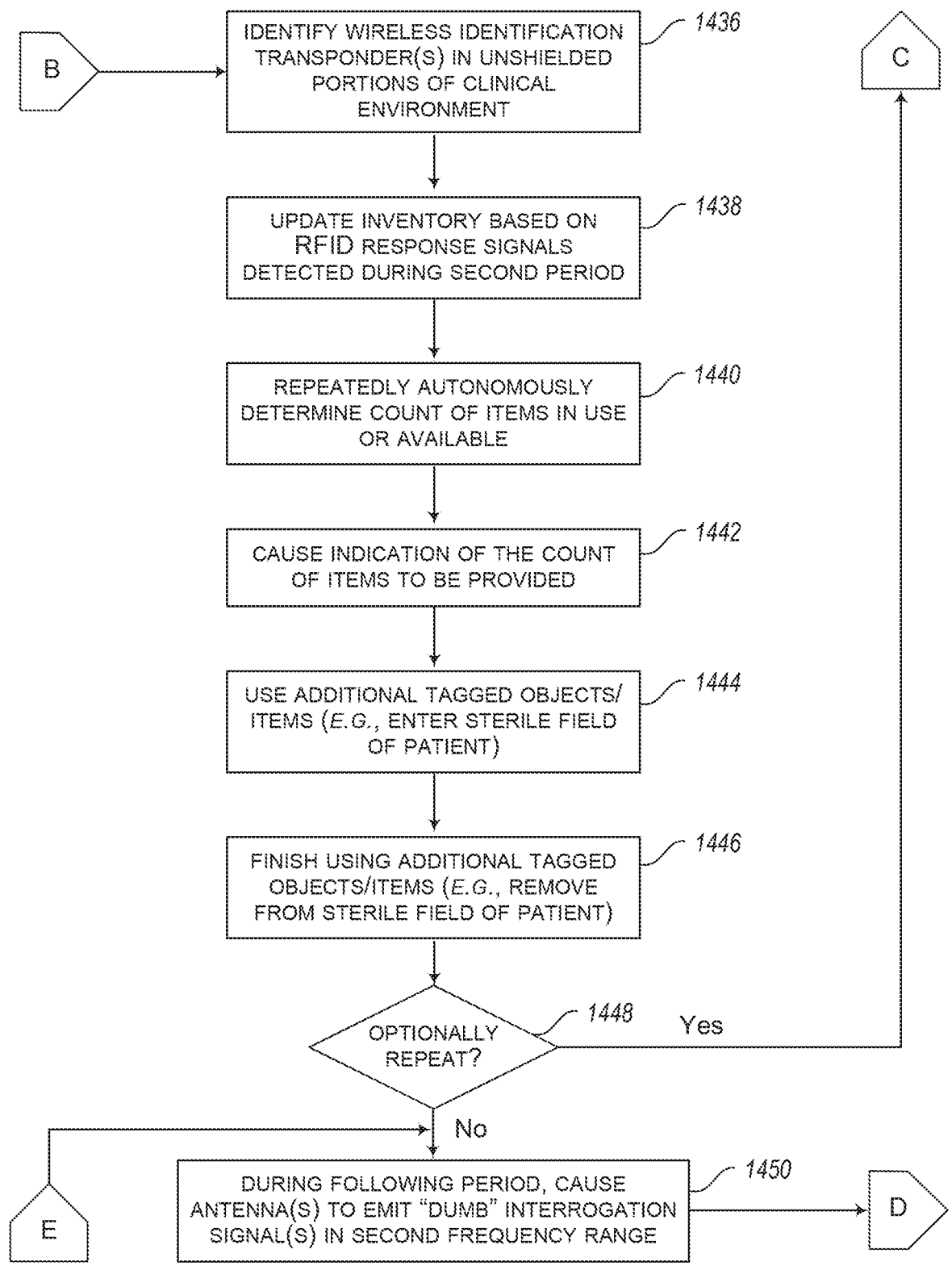
Figure 11D:
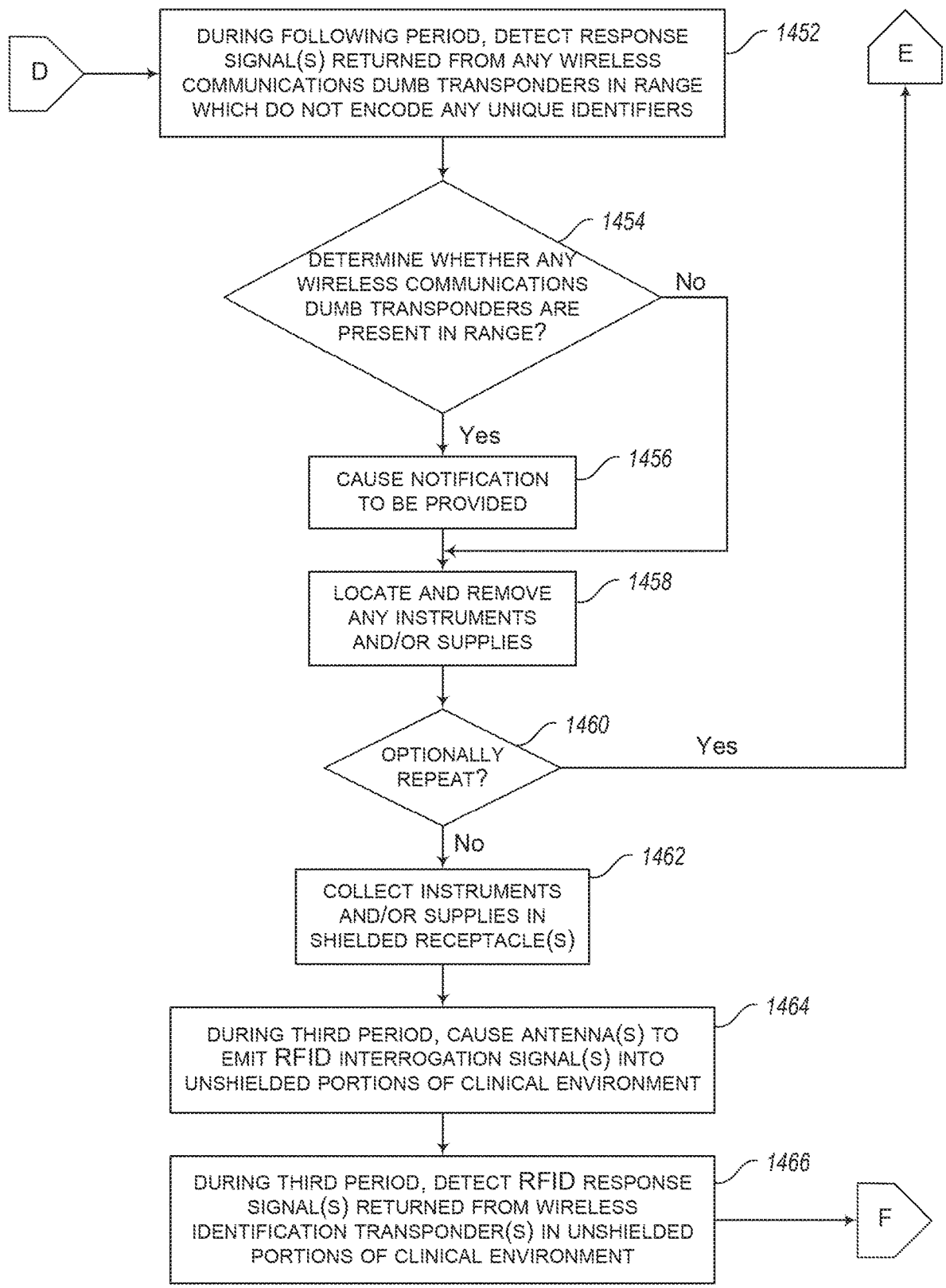
Figure 11E:
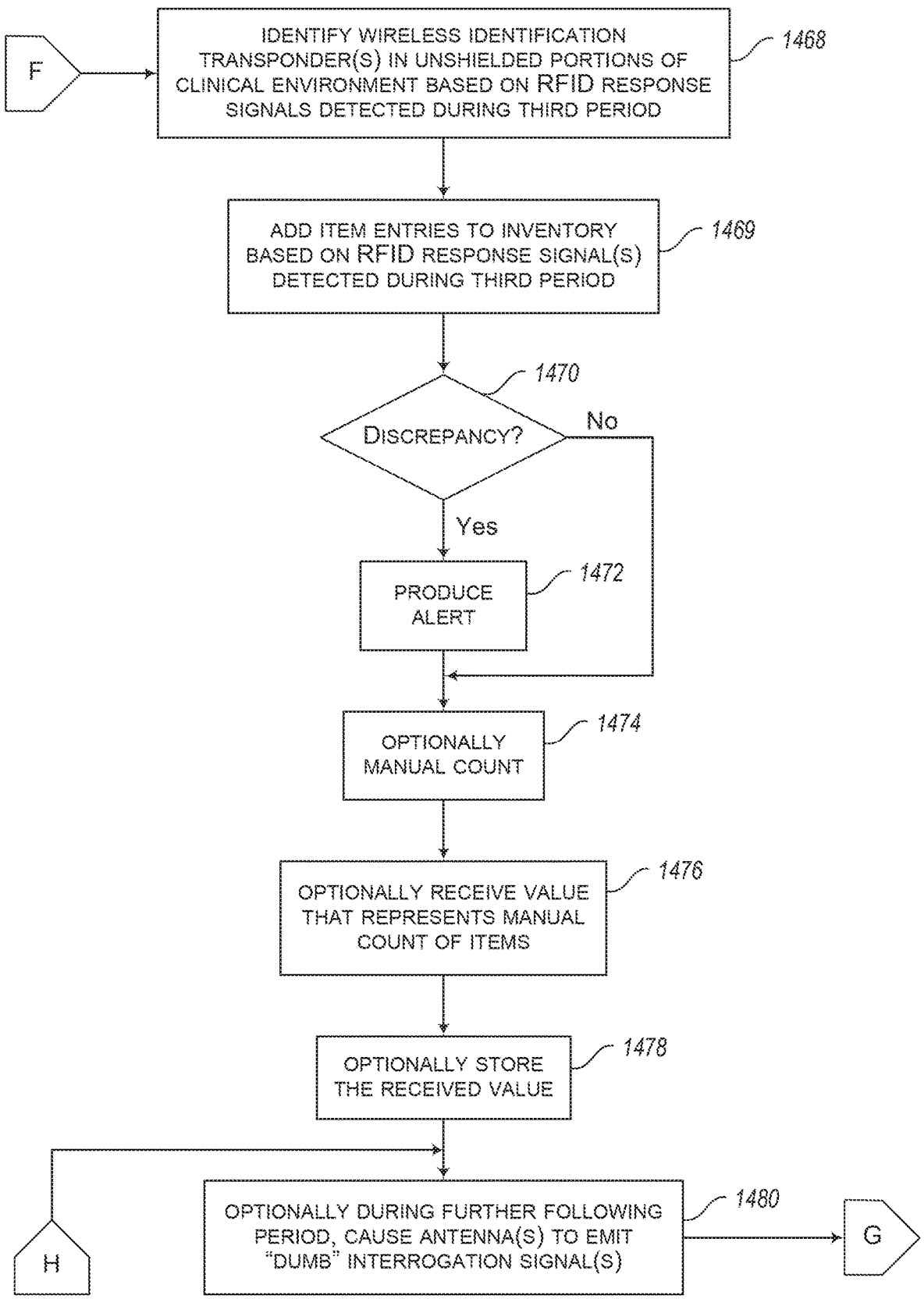
Figure 11F:
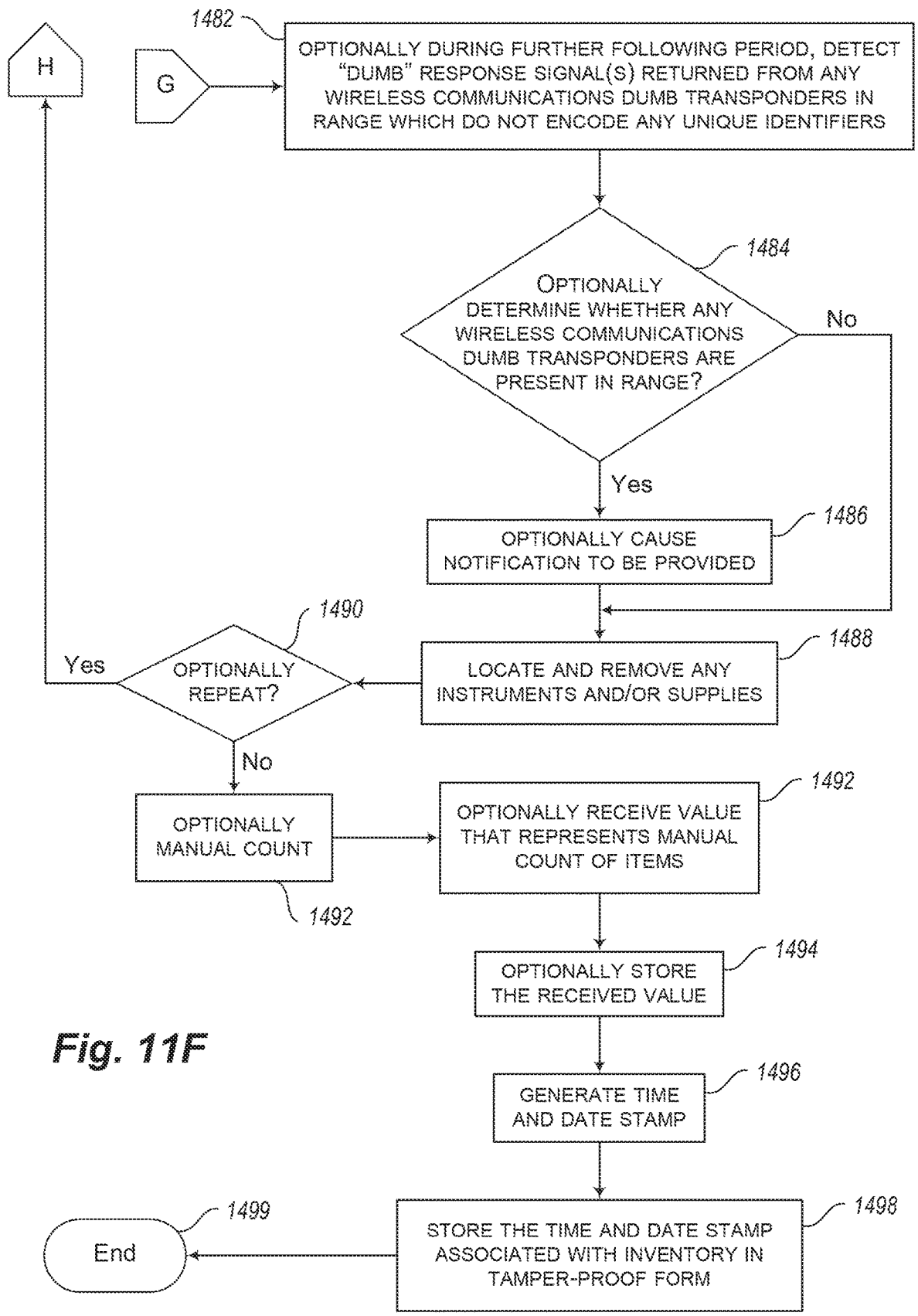

The display 1202 is communicatively coupled to the processor-based system 1304 (FIG. 10). The processor-based system 1304 (FIG. 10) is configured to control the images displayed on the display 1202. The display 1202 may provide all, or a portion, of a user interface, for an end user to interact with the microprocessors, memory, nontransitory computer- or processor-readable storage devices. The display 1202 may take the form of a touch panel display, allowing an end user to enter commands or instructions, or otherwise make selections, via a graphical user interface 1214. Alternatively, or additionally, one or more other user input devices may be provided, for instance a keyboard, keypad, mouse, trackball, other pointer control device, or a microphone and voice activated interface.

The graphical user interface 1214 may include one or more menus 1216. The menus 1216 may include icons 1216a-1216e corresponding to specific functions or operational modes which may be selected. A specific function or mode may be selected by touching the appropriate portion of the user interface or placement of a cursor over the appropriate portion of the user interface. In response, a set of related icons may be displayed for instance by way of a pull-down menu or dialog box. Such may allow further selections or configuration of the specific mode or function. Icons 1216a-1216e for some exemplary functions or operational modes are illustrated. Selection of a checking function or mode 1216a causes the accounting system 1200 to check medical procedure related instruments and supplies in and out in a database. Selection of a patient function or mode icon 1216b may allow patient-specific information to be viewed and/or recorded or modified. Selection of an equipment function or mode 1216c may allow the end user to read information or data produced or collected by various pieces of medical equipment on the display 1202, for instance, blood pressure, heart rate, temperature, blood oxygen levels, respiration, electrocardiogram, etc. The equipment function or mode may additionally, or alternatively, allow an end user to configure parameters of a piece of medical equipment via the user interface. Selection of the symbol reading function or mode icon 1216d may allow use of a machine-readable symbol reader (not shown in FIG. 9), while the selection of the RFID reading function or mode icon 1216e may allow the use of an RFID interrogator or reader 140 (FIG. 1) or presence/absence interrogation system(s) 122 (FIG. 1).

The graphical user interface 1214 may have one or more windows or panels 1218 (only one illustrated) that present or display information. Multiple windows or panels 1218 may be displayed at the same time, or individual windows or panels 1218 may be displayed one by one, for example in response to a user selection of a particular function or mode or selection of a particular window or panel 1218.

The illustrated window or panel 1218 is related to a medical procedure related object accounting mode or function that checks medical procedure related instruments and supplies in and out in a data store (e.g., database) stored in at least one computer- or processor-readable storage medium, hence is also denominated as a checking mode or function.

In the accounting or checking mode or function, the accounting system 1200 determines which medical procedure related instruments 108 (FIG. 1) and supplies 110 (FIG. 1) are present in at least some portions (e.g., unshielded portions, shielded portions) of medical or clinical environment 100 just prior to or at a start of a medical or clinical procedure. The accounting system 1200 also determines which medical procedure related instruments 108 and supplies 110 are present in at least some portions (e.g., unshielded portions, shielded portions) of medical or clinical environment 100 just prior to or at an end a medical or clinical procedure. The accounting system 1200 may optionally determine which medical procedure related instruments 108 and supplies 110 are present in at least some portions (e.g., unshielded portions, shielded portions) of medical or clinical environment 100 at intervals during the medical procedure between the start and the end of the medical or clinical procedure, for example from time to time, periodically or even continuously. The accounting system 1200 may make such determinations based, for example, on unique identifiers read from one or more RFID transponders by one or more RFID interrogators or readers 140 (FIG. 1).

As previously noted, the RFID interrogator(s) or reader(s) 140 can transmit interrogation signals from one or more antennas 146 (FIG. 1), to excite, power or otherwise cause wireless communications identification or RFID transponders 124*b* (FIG. 1) to transmit or emit a response signal. One or more antennas 146 may receive the response signals from the excited or powered RFID transponders 124*b*. The RFID interrogator(s) or reader(s) 140 and/or the accounting system 1200 may decode the received response signals to determine identifying information encoded therein. The RFID interrogator(s) or reader(s) 140 and/or the accounting system 1200 may logically associate each RFID transponder 124*b* with an item (e.g., instrument 108, supply 110) to which the respective RFID transponder 124*b* is physically attached.

The accounting system 1200 may catalog the medical or clinical procedure related instruments 108 and supplies 110 that are present based on the identifying information. For example, the response signals may contain unique identifiers stored or hardcoded into the RFID transponders 124*b*. These unique identifiers may be mapped to information about the respective instruments 108 and/or supplies 110, for instance in a data store (e.g., database). Alternatively, information about the respective instruments 108 and/or supplies 110 may be stored in the transponder and encoded in the response signals. Such information may include the name or identity of the instrument 108 or supply 110, a manufacturer identification, model identification, date put in use, date refurbished or sharpened, date sterilized, method of sterilization, history of use, etc. Such allows tracking and/or tracking of instruments 108 and supplies 110, before, during and after use.

The accounting system 1200 may display information related to the status of the various instruments 108 and/or supplies 110 in a chart 1218 or other format. For example, the chart 1218 may include an entry, for instance a row 1220 (only one called out in FIG. 9), for each instrument 108 and supply 110 present proximate a start of the medical procedure. The instrument 108 or supply 110 may be identified by an identifier 1222, for instance a non-unique commonly recognized name or description. A current status of the instrument 108 or supply 110 may be identified by an appropriate status indicator 1224 (e.g., In/Out, Present/Absent). Optionally, a unique identifier associated with the instrument 108 or supply 110 may be identified by an appropriate indicator 1226 (e.g., unique identifier provided by an RFID transponder physically attached to the instrument 108 or supply 110). Optionally, "last seen" information identifying a time and date that the instrument 108 or supply 110 was last identified may be provided via an appropriate indicator 1228 (e.g., October 12 at 9:32 AM). A scroll bar 1230 or similar graphical user interface tool may be provided to allow a user to review information for a large number of instruments 108 and supplies 110.

The accounting system 1200 may determine if there is a discrepancy between the medical or clinical procedure related objects that were present at or proximate a start and at or proximate an end of the medical or clinical procedure. The accounting system 1200 may provide a suitable warning or notification 1232 if a discrepancy exists, and/or if a discrepancy does not exist. While illustrated as a visual notification, an aural and/or tactile notification may additionally or alternatively be supplied.

The graphical user interface 1214 may include one or more icons 1234 (only one illustrated), user selection of which may cause certain actions. For instance, selection of an update icon 1234 may cause the accounting system 1200 to cause a rescan or re-interrogation of the medical or clinical procedure environment 100, or portions thereof, to account for the presence, absence or location of various medical or clinical procedure related instruments 108 and tools 110.

FIG. 10 and the following discussion provide a brief, general description of a suitable processor system 1304 in which the various illustrated embodiments, as well as other embodiments can be implemented. The processor system 1304 can for example implement the wireless presence/absence interrogation systems 122 (FIG. 1). Additionally, or alternatively, processor system 1304 can for example implement the accounting system 130 (FIG. 1), 1200 (FIG. 9). Although not required, some portion of the embodiments will be described in the general context of computer-executable instructions or logic, such as program application modules, objects, functions, procedures or macros being executed by a computer or processor. Those skilled in the relevant art will appreciate that the illustrated embodiments as well as other embodiments can be practiced with other computer- or processor-based system configurations, including handheld devices, multiprocessor systems, microprocessor-based or programmable consumer electronics, personal computers ("PCs"), network PCs, minicomputers, mainframe computers, and the like. The embodiments can be practiced in distributed computing environments where tasks or modules are performed by remote processor-based devices, which are linked through a communications network. In a distributed computing environment, program modules may be located in local and/or remote memory storage devices, for instance in the cloud. Network connections allow for cloud computing and/or cloud storage.

The processor system 1304 may take the form of a conventional personnel computer (PC), which includes one or more processors 1306, system memories 1308 and system buses 1310 that couple various system components including the system memory 1308 to the processor 1306. The processor system 1304 and its components will at times be referred to in the singular herein, but this is not intended to limit the embodiments to a single system or single components, since in certain embodiments, there will be more than one system or other local or remote networked computing device or multiple instances of any component involved. Unless described otherwise, the construction and operation of the various blocks shown in FIG. 10 are of conventional design. As a result, such blocks need not be described in further detail herein, as they will be understood by those skilled in the relevant art.

The processor 1306 may be any logic processor, such as one or more central processor units (CPUs), microprocessors, digital signal processors (DSPs), application-specific integrated circuits (ASICs), field programmable gate arrays (FPGAs), etc.

As described in applicant's prior applications, the processor 1306 may take the form of a soft processor core, such as that supplied by XILINX under the name MICROBLAZE™ which implements a 32-bit processor including memory caches and a floating point unit. A soft core processor is one that is implemented by interconnected FPGA logic cells instead of by a traditional processor logic. The processor core may be connected to the internal FPGA peripherals using a 32-bit processor bus called the On-Chip Peripheral Bus. The XILINX supplied peripherals for the MICROBLAZE™ processor core include external memory interfaces, timers, and general purpose I/O. Custom logic to create the transmit signals, sample the ADC, and accumulate the transponder return signals may be designed as a peripheral to the soft processor core. The custom logic may be part of the design of the FPGA.

Alternatively, the processor 1306 may take the form of a full microprocessor. Non-limiting examples of commercially available microprocessors include, but are not limited to, an 80×86 or Pentium series microprocessor from Intel Corporation, U.S.A., a PowerPC microprocessor from IBM, a Sparc microprocessor from Sun Microsystems, Inc., a PA-RISC series microprocessor from Hewlett-Packard Company, or a 68xxx series microprocessor from Motorola Corporation. For example, the processor 1306 may take the form of a full microprocessor such as the ATOM™ processor, commercially available from Intel Corporation. The full microprocessor may be communicatively coupled to multiple analog antenna channels, for example via one or more plug-in boards 1364a, 1364b (collectively 1364, only two shown) which carry respective FPGAs and one or more suitable buses. The FPGA may, for example, act as a co-processor and/or cache. For example, the plug-in boards 1364 may implement or carry the circuits disclosed in U.S. patent application Ser. No. 11/759,141 filed Jun. 6, 2007, U.S. Provisional Patent Application Ser. No. 61/056,787 filed May 28, 2008, and U.S. Provisional Patent Application Ser. No. 61/091,667 filed Aug. 25, 2008, with or without change, which patent applications are incorporated herein by reference in their entirety.

The system bus 1310 can employ any known bus structures or architectures, including a memory bus with memory controller, a peripheral bus, and a local bus. A relatively high bandwidth bus architecture may be employed. For example, a PCI Express™ or PCIe™ bus architecture may be employed, rather than an ISA bus architecture. Suitable FPGAs may include those from ATMEL Corporation. Such FPGAs may advantageously have built in PCIe bus architecture, allowing easy integration. This approach may enable more I/O ports, such as USB ports, may provide more or better video options, and may provide faster data rates from the analog antenna channels than otherwise possible using the ISA bus architecture and a soft processor core approach. Some embodiments may employ separate buses for data, instructions and power.

The system memory 1308 includes read-only memory ("ROM") 1312 and random access memory ("RAM") 1314. A basic input/output system ("BIOS") 1316, which can form part of the ROM 1312, contains basic routines that help transfer information between elements within the processor system 1304, such as during start-up.

The processor system 1304 also includes a hard disk drive 1318 for reading from and writing to a magnetic hard disk 1320, an optical disk drive 1322 for reading from and writing to removable optical disks 1326, and a removable disk drive 1324 for reading from and writing to removable disks 1328. The optical disk 1326 can be a CD or a DVD, etc., while the removable magnetic disk 1328 can be a magnetic floppy disk or diskette. The hard disk drive 1318, optical disk drive 1322 and removable disk drive 1324 communicate with the processor 1306 via the system bus 1310. The hard disk drive 1318, optical disk drive 1322 and removable disk drive 1324 may include interfaces or controllers (not shown) coupled between such drives and the system bus 1310, as is known by those skilled in the relevant art. Additionally or alternatively, the processor system 1304 may include one or more solid state drives (SSD). The drives 1318, 1322, 1324, and their associated computer-readable media 1320, 1326, 1328, provide nonvolatile storage of computer-readable instructions, data structures, program modules and other data for the processor system 1304. Although the depicted processor system 1304 employs hard disk 1320, optical disk 1326 and removable disk 1328, those skilled in the relevant art will appreciate that other types of computer-readable media that can store data accessible by a computer may be employed, such as magnetic cassettes, flash memory cards, Bernoulli cartridges, RAMs, ROMs, smart cards, etc.

Program modules can be stored in the system memory 1308, such as an operating system 1330, one or more application programs 1332, other programs or modules 1334, drivers 1336 and program data 1338.

The application programs 1332 may, for example, include interrogation logic 1332a, check in/out logic 1332b, and machine-readable symbol reading logic 1332c, as well as another other peripheral logic 1332d associated with operating a non-reader device, referred to in FIG. 10 and elsewhere herein as peripheral logic and peripheral device, respectively. The logic 1332a-1332d may, for example, be stored as one or more executable instructions. The interrogation logic 1332a may include logic or instructions to cause antenna(s) 142 (FIG. 1) and/or RFID interrogator(s) 140 (FIG. 1) to transmit wireless interrogation signals, receive response signals to the interrogations signals, and in the case of RFID transponders decode information encoded in the response signals, for instance unique identifiers stored in RFID transponders. Such may encode information in the interrogation signals, for instance information to be encoded in an RFID transponder. The check in/out logic 1332b may include logic to monitor or track a status of various medical procedure instruments and supplies. Such may, for example, update information in a data store (e.g., database) stored on one or more computer- or processor-readable storage media. Such may also allow the generation of queries and retrieval of information from such data store. Such may, for example, update create a record or field in the database for each medical procedure instrument or supply that is present in at least unshielded portions of the medical or clinical environment 100 (FIG. 1) before or at the start of a medical procedure. Such may also, for example, update a respective record or field of the data store or database if a medical procedure instrument or supply is removed from at least unshielded portions of the medical or clinical environment 100 (FIG. 1). Such may also, for example, update a respective record or field of the data store or database if the medical instrument or supply reappears in at least unshielded portions of the medical or clinical environment 100 (FIG. 1) during the medical or clinical procedures.

Such may take the form of identifying a particular instrument as being checked in if detected in at least unshielded portions of the medical or clinical environment 100 (FIG. 1), and otherwise identifying the particular instrument as checked out. A query may be run, either from time to time or before ending a medical or clinical procedure, to ensure that all the medical or clinical instruments and supplies present at the start of the medical or clinical procedure are present and accounted for at the end of the medical procedure. In some implementations, all instruments and supplies are placed in shielded portions (e.g., shielded receptacles) at or proximate the end of the medical or clinical procedure, and the medical or clinical environment is interrogated to determine that no response signals are received. This ensures that no medical instruments or supplies are left behind in a body of a patient undergoing a medical or clinical procedure.

The machine-readable symbol reading logic 1332c may allow the capture and decoding of information encoded in machine-readable symbols, such as barcode symbols, area or matrix code symbols and/or stacked code symbols. Such logic is commonly found in dedicated machine-readable symbol readers. The peripheral logic 1332*d* can be any logic loaded into or otherwise stored in a computer- or processor-readable storage medium. The peripheral logic 1332*d* allows operation of a peripheral device, such as a non-reader type device. For instance, the peripheral logic 1332*d* may collect data from one or more pieces of medical procedure equipment (e.g., cautery equipment, heart-lung machine, ablation system, anesthesia deliver apparatus) or medical procedure sensors (e.g., electrode, pulse-oximetry sensor, blood pressure sensor, temperature probe, heart monitor), or other data collection devices. Interrogation logic 1332*a*, machine-readable symbol reading logic 1332*c*, and/or peripheral logic 1332*d* may be automatically loaded into one or more computer- or processor-readable storage medium in response to the communicative coupling of a respective device to the presence/absence interrogator or reader 1360*a*, 1360*b*. Such may advantageously provide plug and play functionality for a wide variety of devices.

The system memory 1308 may also include communications programs 1340, for example a server and/or a Web client or browser for permitting the processor system 1304 to access and exchange data with other systems such as user computing systems, Web sites on the Internet, corporate intranets, extranets, or other networks as described below. The communications programs 1340 in the depicted embodiment is markup language based, such as Hypertext Markup Language (HTML), Extensible Markup Language (XML) or Wireless Markup Language (WML), and operates with markup languages that use syntactically delimited characters added to the data of a document to represent the structure of the document or to format information. A number of servers and/or Web clients or browsers are commercially available such as those from Mozilla Corporation of California and Microsoft of Washington.

While shown in FIG. 10 as being stored in the system memory 1308, the operating system 1330, application programs 1332, other programs/modules 1334, drivers 1336, program data 1338 and server and/or browser 1340 can be stored on the hard disk 1320 of the hard disk drive 1318, the optical disk 1326 of the optical disk drive 1322 and/or the magnetic disk 1328 of the magnetic disk drive 1324. A user can enter commands and information into the processor system 1304 through input devices such as a touch screen or keyboard 1342 and/or a pointing device such as a mouse 1344. Other input devices can include a microphone, joystick, game pad, tablet, scanner, biometric scanning device, etc. These and other input devices are connected to the processor 1306 through an interface 1346 such as a universal serial bus ("USB") interface, Firewire, and/or optical Firewire interface, that couples to the system bus 1310, although other interfaces such as a parallel port, a game port or a wireless interface or a serial port may be used. A monitor 1348 or other display device is coupled to the system bus 1310 via a video interface 1350, such as a video adapter. Although not shown, the processor system 1304 can include other output devices, such as speakers, printers, etc.

The processor system 1304 operates in a networked environment using one or more of the logical connections to communicate with one or more remote computers, servers and/or devices via one or more communications channels, for example, one or more networks 1352. These logical connections may facilitate any known method of permitting computers to communicate, such as through one or more LANs and/or WANs, such as the Internet, intranet, cloud and/or extranet. Such networking environments are well known in wired and wireless enterprise-wide computer networks, intranets, extranets, and the Internet. Other embodiments include other types of communication networks including telecommunications networks, cellular networks, paging networks, and other mobile networks.

When used in a WAN networking environment, the processor system 1304 may include a modem or wireless hotspot 1354 for establishing communications over a WAN, for instance the Internet. The modem 1354 is shown in FIG. 10 as communicatively linked between the interface 1346 and the network 1352. Additionally or alternatively, another device, such as a network port 1356, that is communicatively linked to the system bus 1310, may be used for establishing communications over the network 1352.

One or more interfaces or ports 1358*a*-1358*n* (collectively 1358, only three illustrated) that are communicatively linked to the system bus 1310, may be used for establishing communications over a WAN, LAN, parallel or serial cable, AC wiring (e.g., ZigBee® protocol transceiver), or wirelessly (e.g., WI-FI® radio, Bluetooth® radio). In some embodiments, the interfaces or ports 1358 may take the form of USB ports allowing communication via respective USB cables. Such may allow a variety of equipment to communicate with the processor system 1304. For example, such may allow communicative coupling with one or more RFID interrogators or readers 1360*a*, machine-readable symbol readers 1360*b* (e.g., machine-readable symbol scanners or imagers), and peripheral equipment 1360*n* (collectively 1360, only three illustrated). The readers 1360*a*, 1360*b* may be configured to transmit pre-processed information to the processor system 1304, for instance identifiers read from RFID transponders or optical symbols (e.g., printed or inscribed markings). The processor system 1304 may be configured to use such information. For instance, the processor system 1304 may be configured to check medical procedure instruments and supplies in and out in the database based on identifiers reader by the readers 1360*a*, 1360*b*. Additionally, or alternatively, the processor system 1304 may be configured to control or otherwise send instructions and/or data to the readers 1360*a*. 1360*b*. Likewise, the processor system 1304 may be configured to check medical procedure instruments and supplies in and out in the database based on information received from the peripheral equipment 1360*c*. Additionally, or alternatively, the processor system 1304 may be configured to control or otherwise send instructions and/or data to the peripheral equipment 1360*c*.

One or more interfaces or slot connectors 1362*a*-1362*n* (collectively 1362, only three illustrated) may allow the communicative coupling of plug-in boards 1364*a*, 1364*b* (collectively 1364, only two illustrated) to the processor system 1304. There may, for example, be one plug-in board 1362 for each antenna 1366*a*, 1366*b* (collectively 1366, only two illustrated, each of the antennas 1366 and plug-in boards 1364 constituting a separate channel. The slot connectors 1362 may allow expansion or use with different antenna configurations. The plug-in boards 1364 may each carry one or more circuits (e.g., analog and/or digital circuit components) configured to transmit interrogation signals from the respective antenna 1366 and to monitor the antenna 1366 for responses to the interrogation signals. For example, the plug-in boards 1364 may implement or carry the circuits disclosed in U.S. patent application Ser. No. 11/759,141 filed Jun. 6, 2007, U.S. Provisional Patent Application Ser. No. 61/056,787 filed May 28, 2008, and U.S. Provisional Patent Application Ser. No. 61/091,667 filed Aug. 25, 2008, with or without change, which patent applications are incorporated herein by reference in their entirety. Processor system 1304 may automatically recognize and be configured in response to a plug-in board 1364 being coupled to an interface or slot connector 1362, for example in a fashion similar to the coupling of a USB device to a computer system.

The processor system 1304 may include one or more synchronization circuits or logic (not shown) configured to control and synchronize the operation of the various plug-in boards 1364. The synchronization circuit or logic may be configured to cause one of the plug-in boards 1364 to transmit an interrogation signal from a first antenna, and cause one or more of the other plug-in boards 1364 to monitor for a response by a transponder to the interrogation signal. For instance, the synchronization circuit or logic may cause the plug-in boards 1364 to monitor all of the antennas 1366 for a response to the interrogation signal. Alternatively, the synchronization circuit or logic may cause the plug-in boards 1364 to have all of the antennas 1366 other than the antenna that transmitted a most recent interrogation signal monitor for a response. Such may advantageously allow monitoring sooner than would otherwise be possible since such can avoid the need to allow the transmitting antenna to return to a quiescent state after transmitting before monitoring for a response. The synchronization circuit or logic may synchronize the plug-in boards 1364 to successively cause the various antennas to transmit, for example starting with an antenna at one end, and successively transmitting from each of the antennas in a defined order. As a further alternative, the synchronization circuit or logic may synchronize the plug-in boards 1364 to cause the transmission of interrogations signals from a subset of the total set of antennas. While illustrated as removably coupled to the processor system 1304, the plug-in boards 1364 could be an integral unitary part thereof. For example, the various antennas may be controlled by respective circuits integrated into a signal circuit board. Alternatively, the various antennas may be controlled by a single circuit. While sequential interrogation is described, some implementations may employ parallel interrogation. Whether sequential or parallel interrogation is employed, the processor system 1304 may employ serial or parallel processing of information.

In a networked environment, program modules, application programs, or data, or portions thereof, can be stored in a server computing system (not shown) or in the cloud. Those skilled in the relevant art will recognize that the network connections shown in FIG. 10 are only some examples of ways of establishing communications between computers, and other connections may be used, including wirelessly.

For convenience, the processor 1306, system memory 1308, network port 1356, interface 1346, interfaces or ports 1358 and connector slots 1362 are illustrated as communicatively coupled to each other via the system bus 1310, thereby providing connectivity between the above-described components. In alternative embodiments of the processor system 1304, the above-described components may be communicatively coupled in a different manner than illustrated in FIG. 10. For example, one or more of the above-described components may be directly coupled to other components, or may be coupled to each other, via intermediary components (not shown). In some embodiments, system bus 1310 is omitted and the components are coupled directly to each other using suitable connections.

FIGS. 11A-11F show a method 1400 of operating a medical procedure object accounting system to account for, track or monitor medical procedure instruments and supplies, according to one illustrated embodiment. The method 1400 can, for example, be implemented by the structures of FIG. 1, which includes one or more receptacles without a receptacle reader, and optionally includes scanning for a presence or absence of dumb transponders in a body of a patient.

The method 1400 starts at 1402, for example on power ON of one or more components (e.g., accounting system, RFID interrogators or readers, presence/absence interrogators or readers), on invocation of some calling program, routine, subprogram or function, or for example in response to detection of motion via a suitable motion sensor (e.g., one- or multi-axis accelerometer).

Optionally, the method may start in a preparation period, by electronically scanning a medical or clinical procedure environment to the presence of objects tagged with a wireless communications transponder. This establishes a baseline, ensuring that the environment is clear of instruments and/or supplies left over from a previous procedure.

At 1401, during a preparation period, antenna(s) of an RFID interrogation system emit RFID interrogation signal(s) into unshielded portions of the clinical environment. The RFID interrogation signals are typically in a first frequency range (e.g., UHF), which is typically a relatively higher frequency than a frequency of the dumb interrogation signals. Such can occur automatically, via autonomous control by an RFID interrogator, or alternatively via manual operation of an RFID interrogator by the personnel. Typically, the RFID interrogation system will emit RFID interrogation signal(s) via a number of room antennas, positioned and/or oriented about a room to provide complete or substantial (i.e., 85%) coverage of all unshielded portions of the room. Alternatively, any one or more of various other RFID interrogators and associated antennas described herein can be employed, for example hand-held RFID interrogators and/or associated antennas, body-worn RFID interrogators and/or associated antennas, mat-based RFID interrogators and/or associated antennas, etc. The preparation period may, for example, be before a start of the medical or clinical procedure, for example as a medical or clinical environment is being readied for a medical or clinical procedure.

At 1403, during the preparation period, one or more RFID interrogators or readers detect RFID response signal(s) returned from wireless identification transponder(s) in unshielded portions of the clinical environment.

At 1405, one or more RFID interrogators or readers determine whether an wireless identification transponder(s) are detected in at least the unshielded portions of the medical or clinical environment based on RFID response signals detected during the preparation period.

At 1407, in response to detection of one or more wireless identification transponders present within its range, RFID interrogators or readers cause a notification to be provided. The notification can, for example, take the form of a visual and/or aural alert. Such can be provided via a display monitor, speakers and/or a heads up or head-worn device, e.g., a virtual reality or augmented reality head set. If detected, the identity of such wireless identification transponders and/or instruments or supplies may be electronically recorded to nontransitory computer- or processor-readable media.

At 1404, at or proximate a start of a medical or clinical procedure, personnel (e.g., supply nurse) opens one or more shielded packages (e.g., packets or envelopes, totes or trays), removing instruments or supplies (e.g., surgical sponges, gauze or pads) in preparation for the medical or clinical procedure.

Optionally at 1406, the personnel (e.g., supply nurse) perform a manual count (e.g., "manual count in") of instruments or supplies (e.g., surgical sponges, gauze or pads) in preparation for the medical or clinical procedure.

Optionally at 1408, an accounting system receives a value that represents the manual count in of instruments or supplies (e.g., surgical sponges, gauze or pads). For example, the personnel may manually enter the count via a keyboard, keypad, or graphical user interface of a computer, for example a desktop computer, laptop computer, tablet computer or smartphone.

Optionally at 1410, the accounting system stores the received value of the count to at least one nontransitory computer- or processor-readable medium. For example, the accounting system may update a field of a record associated with or corresponding to the particular instrument, supply or RFID transponder physically associated therewith.

At 1412, during a first period, antenna(s) of an RFID interrogation system emit RFID interrogation signal(s) into unshielded portions of the clinical environment. The RFID interrogation signals are typically in a first frequency range, which is typically a relatively higher frequency than a frequency of the dumb interrogation signals. Such can occur automatically, via autonomous control by an RFID interrogator, or alternatively via manual operation of an RFID interrogator by the personnel. Typically, the RFID interrogation system will emit RFID interrogation signal(s) via a number of room antennas, positioned and/or oriented about a room to provide complete or substantial (i.e., 85%) coverage of all unshielded portions of the room. Alternatively, any one or more of various other RFID interrogators and associated antennas described herein can be employed, for example hand-held RFID interrogators and/or associated antennas, body-worn RFID interrogators and/or associated antennas, mat-based RFID interrogators and/or associated antennas, etc. The first period may, for example, be at or proximate a start of the medical or clinical procedure.

At 1414, during the first period, one or more RFID interrogators or readers detect RFID response signal(s) returned from wireless identification transponder(s) in unshielded portions of the clinical environment.

At 1416, one or more RFID interrogators or readers identify wireless identification transponder(s) in unshielded portions of the medical or clinical environment based on RFID response signals detected during the first period. In some implementations, various instruments or supplies with associated RFID transponders may be passed by antennas of an RFID interrogator, one at a time and read sequentially. In other implementations, an RFID interrogator may query a group of instruments and/or supplies using various singulation techniques to read identifying information from the respective RFID transponders physically attached to each instrument and/or supply.

At 1418, the accounting system adds item entries for each instrument and/or supply (e.g., automatic count in) to an inventory based on the various RFID response signal(s) detected during the first period, for instance in response to receipt of information from one or more RFID interrogators or readers. For example, the accounting system may update a field of a record associated with or corresponding to the particular instrument, supply or RFID transponder physically associated therewith.

Optionally, the accounting system or some other component, determines a count of items in use or available, and/or causes an indication of the count of items to be provided, similar or even identical as performed at 1540, 1542 described below. Such can occur repeatedly, either continuously, periodically, aperiodically, or on demand, throughout a procedure. The inventory can be maintained locally or remotely.

At 1420, a medical care provider uses various ones of the instruments and/or supplies during the medical or clinical procedure, typically introducing the instruments and/or supplies into a sterile field of a patient.

At 1422, the medical care provider finishes using various ones of the instruments and/or supplies during the medical or clinical procedure, typically removing the instruments and/or supplies from the sterile field of the patient.

At 1424, personnel (e.g., supply nurse) open one or more additional shielded packages (e.g., packets or envelopes, totes or trays), removing instruments or supplies (e.g., surgical sponges, gauze or pads).

Optionally at 1426, the personnel (e.g., supply nurse) perform a manual count (e.g., "manual count in") of the additional instruments or supplies (e.g., surgical sponges, gauze or pads).

Optionally at 1428, the accounting system receives a value that represents the manual count of additional instruments or supplies (e.g., surgical sponges, gauze or pads). For example, the personnel may manually enter the count via a keyboard, keypad, or graphical user interface of a computer, for example a desktop computer, laptop computer, tablet computer or smartphone.

Optionally at 1430, the accounting system stores the received value of the count to at least one nontransitory computer- or processor-readable medium. For example, the accounting system may update a field of a record associated with or corresponding to the particular instrument, supply or RFID transponder physically associated therewith.

At 1432, during the second period, antenna(s) emit RFID interrogation signal(s) into unshielded portions of the medical or clinical environment. Such can occur automatically, via autonomous control by an RFID interrogator, or alternatively via manual operation of an RFID interrogator by the personnel. Typically, the RFID interrogation system will emit RFID interrogation signal(s) via a number of room antennas, positioned and/or oriented about a room to provide complete or substantial (i.e., 85%) coverage of all unshielded portions of the room. Alternatively, any one or more of various other RFID interrogators and associated antennas described herein can be employed, for example hand-held RFID interrogators and/or associated antennas, body-worn RFID interrogators and/or associated antennas, mat-based RFID interrogators and/or associated antennas, etc.

At 1434, during the second period, one or more RFID interrogators detect RFID response signal(s) returned from wireless identification transponder(s) in unshielded portions of the medical or clinical environment.

At 1436, one or more RFID interrogations identify wireless identification transponder(s) in unshielded portions of the medical or clinical environment based on RFID response signals detected during the second period. In some implementations, various instruments or supplies with associated RFID transponders may be passed by antennas of an RFID interrogator, one at a time and read sequentially. In other implementations, an RFID interrogator may query a group of instruments and/or supplies using various singulation techniques to read identifying information from the respective RFID transponders physically attached to each instrument and/or supply.

At 1438, the accounting system updates the inventory based on the various RFID response signals detected during the second period. For example, the accounting system may update a field of a record associated with or corresponding to the particular instrument, supply or RFID transponder physically associated therewith.

Optionally at 1440, the accounting system or some other component repeatedly determines a count of items in use or available. Such can occur autonomously by the accounting system or some other component.

Optionally at 1442, the accounting system or some other component causes an indication of the count of items to be provided. Such can include producing a visual display of the count on a display device (e.g., monitor, heads up or head-worn display such as Oculus Rift or Google Glass).

At 1444, a medical care provider uses various ones of the additional instruments and/or supplies during the medical or clinical procedure, typically introducing the instruments and/or supplies into a sterile field of a patient.

At 1446, the medical care provider finishes using various ones of the additional instruments and/or supplies used during the medical or clinical procedure, typically removing the instruments and/or supplies from the sterile field of the patient.

At 1448, the acts 1424, 1426, 1428, 1430, 1434, 1436, 1438, 1440, 1442, 1444, and/or 1446 may optionally repeat throughout the medical or clinical procedure.

At 1450, during a following period, one or more antenna(s) optionally emit dumb interrogation signal(s) into unshielded portions of the medical or clinical environment. The dumb interrogation signals are typically in a second frequency range, which is typically a relatively lower frequency than a frequency of the RFID interrogation signals. Such can occur automatically, via autonomous control by one or more presence/absence interrogator, or alternatively via manual operation of one or more presence/absence interrogator by the personnel. Any one or more of the various presence/absence interrogators described herein can be employed.

At 1452, during the following period, one or more presence/absence interrogator optionally detect response signal(s) returned from any wireless communications dumb transponders in range, which wireless communications dumb transponders and response signals do not encode any unique identifiers.

At 1454, one or more presence/absence interrogators optionally determine whether any wireless communications dumb transponders are present in its range during the following period. The one or more presence/absence interrogators can employ any of the various techniques described herein and described in the materials incorporated by reference herein.

At 1456, in response to detection of one or more wireless communications dumb transponders present within its range, the one or more presence/absence interrogators cause a notification to be provided. The notification can, for example, take the form of a visual and/or aural alert. Such can be provided via a display monitor, speakers and/or a heads up or head-worn device, e.g., a virtual reality or augmented reality head set.

At 1458, personnel may locate and remove any instruments and/or supplies associated with the detected wireless communications dumb transponders from the patient (e.g., from the sterile field of the patient).

At 1460, the acts 1450, 1452, 1454, 1456 and/or 1458 may repeat one or more times, for example until no wireless communications dumb transponders are detected in the body of the patient.

At 1462, the personnel (e.g., supply nurse) collect all the instruments and/or supplies in one or more shielded receptacles, and close the shielded receptacle(s) to prevent interrogation of RFID transponders physically attached to any of the instruments and/or supplies in one or more shielded receptacles.

At 1464, during a third period, antenna(s) of an RFID interrogation system emit RFID interrogation signal(s) into unshielded portions of the clinical environment. The RFID interrogation signals are typically in a first frequency range, which is typically a relatively higher frequency than a frequency of the dumb interrogation signals. Such can occur automatically, via autonomous control by an RFID interrogator, or alternatively via manual operation of an RFID interrogator by the personnel. Typically, the RFID interrogation system will emit RFID interrogation signal(s) via a number of room antennas, positioned and/or oriented about a room to provide complete or substantial (i.e., 85%) coverage of all unshielded portions of the room. Alternatively, any one or more of various other RFID interrogators and associated antennas described herein can be employed, for example hand-held RFID interrogators and/or associated antennas, body-worn RFID interrogators and/or associated antennas, mat-based RFID interrogators and/or associated antennas, etc. The third period may, for example, be at or proximate an end of the medical or clinical procedure. The third period follows the first and the optional second periods. The third period may, for example, follow the following period, or may occur before the following period. In this respect, the following period is denominated as such since it follows the first period, and may follow the optional second period.

At 1466, during the third period, one or more RFID interrogators or readers detect RFID response signal(s) returned from wireless identification transponder(s) in unshielded portions of the medical or clinical environment.

At 1468, one or more RFID interrogators or readers identify wireless identification transponder(s) in unshielded portions of the medical or clinical environment based on RFID response signals detected during the third period. In some implementations, various instruments or supplies with associated RFID transponders may be passed by antennas of an RFID interrogator, one at a time and read sequentially. In other implementations, an RFID interrogator may query a group of instruments and/or supplies using various singulation techniques to read identifying information from the respective RFID transponders physically attached to each instrument and/or supply.

At 1469, the accounting system updates item entries for each instrument and/or supply (e.g., automatic count out) to the inventory based on the various RFID response signal(s) detected or not detected during the third period, for instance in response to receipt of information from one or more RFID interrogators or readers. For example, the accounting system may update a field of a record associated with or corresponding to the particular instrument, supply or RFID transponder physically associated therewith.

At 1470, the accounting system determines if a discrepancy exists in the inventory (e.g., count in does not match count out, item unaccounted for, each item checked in not checked out, item located in unshielded portion of medical or clinical procedure environment).

At 1472, the accounting system causes an alert to be provided in response to detection of discrepancy. The alert can, for example, take the form of a visual and/or aural alert. Such can be provided via a display monitor, speakers and/or a heads up or head-worn device, e.g., a virtual reality or augmented reality head set.

Optionally at 1474, the personnel (e.g., supply nurse) perform a manual count (e.g., "manual count out) of instruments or supplies (e.g., surgical sponges, gauze or pads) in preparation for ending (e.g., closing) the medical or clinical procedure.

Optionally at 1476, accounting system receives a value that represents the manual count out of instruments or supplies (e.g., surgical sponges, gauze or pads). For example, the personnel may manually enter the count via a keyboard, keypad, or graphical user interface of a computer, for example a desktop computer, laptop computer, tablet computer or smartphone.

Optionally at 1478, the accounting system stores the received value of the count to at least one nontransitory computer- or processor-readable medium. For example, the accounting system may update a field of a record associated with or corresponding to the particular instrument, supply or RFID transponder physically associated therewith.

Optionally at 1480, during a further following period, one or more antenna(s) emit dumb interrogation signal(s) into unshielded portions of the clinical environment. The dumb interrogation signals are typically in a second frequency range, which is typically a relatively lower frequency than a frequency of the RFID interrogation signals. Such can occur automatically, via autonomous control by one or more presence/absence interrogator, or alternatively via manual operation of one or more presence/absence interrogator by the personnel. Any one or more of the various presence/absence interrogators described herein can be employed.

Optionally at 1482, during the further following period, one or more presence/absence interrogator detect response signal(s) returned from any wireless communications dumb transponders in range, which wireless communications dumb transponders and response signals do not encode any unique identifiers.

Optionally at 1484, one or more presence/absence interrogators determine whether any wireless communications dumb transponders are present in its range during the further following period. The one or more presence/absence interrogators can employ any of the various techniques described herein and described in the materials incorporated by reference herein.

Optionally at 1486, in response to detection of one or more wireless communications dumb transponders present within its range, the one or more presence/absence interrogators cause a notification to be provided. The notification can, for example, take the form of a visual and/or aural alert. Such can be provided via a display monitor, speakers and/or a heads up or head-worn device, e.g., a virtual reality or augmented reality head set.

At 1488, personnel may locate and remove any instruments and/or supplies associated with the detected wireless communications dumb transponders from the patient (e.g., from the sterile field of the patient).

At 1490, the acts 1480, 1482, 1484, 1486 and/or 1488 may repeat one or more times, for example until no wireless communications dumb transponders are detected in the body of the patient.

Optionally at 1491, the personnel (e.g., supply nurse) perform a further, final, manual count (e.g., "manual count out) of instruments or supplies (e.g., surgical sponges, gauze or pads) in preparation for ending (e.g., closing) the medical or clinical procedure.

Optionally at 1492, accounting system receives a value that represents the further, final, manual count out of instruments or supplies (e.g., surgical sponges, gauze or pads). For example, the personnel may manually enter the count via a keyboard, keypad, or graphical user interface of a computer, for example a desktop computer, laptop computer, tablet computer or smartphone.

Optionally at 1494, the accounting system stores the received value of the further final count to at least one nontransitory computer- or processor-readable medium. For example, the accounting system may update a field of a record associated with or corresponding to the particular instrument, supply or RFID transponder physically associated therewith.

Optionally at 1496, the accounting system generates a time and date stamp, indicative of a time and date of the accounting or inventory.

Optionally at 1498, the accounting system or some other component stores the time and date stamp associated with inventory in tamper-proof form. For example, the accounting system can generate a hash based on the accounting and inventory and time and date stamp and store the same, allowing such to be later validated by authorized parties.

The method 1400 terminates at 1499, for example until invoked again. In some implementations, the method 1400 may be executed repeatedly, even continuously, or periodically or aperiodically. The method 1400 can be implemented as multiple threads, for example via a multi-threaded processor.

Transponders useful for marking medical procedure related objects may take a variety of forms. Transponders capable of withstanding sterilization procedures would be particularly advantageous. A permanent memory type RFID transponder which retains information or data, for instance a unique identifier, and which is substantially gamma ray resistant and capable of being subjected to the relatively high temperatures often associated with sterilization may be formed from an antenna, passive power or backscatter circuit and a permanent memory circuit communicatively coupled to the antenna and powered via the passive power or backscatter circuit to transmit the contents of the permanent memory in response to power derived from an interrogation signal. The permanent memory circuit may advantageously take the form or may incorporate aspects of the permanent memory circuits described in one or more of U.S. Pat. Nos. 7,609,538; 7,471,541; 7,269,047; 7,042,722; 7,031,209; 6,992,925; 6,972,986; 6,956,258; 6,940,751; 6,898,116; 6,856,540; 6,822,888; 6,798,693; 6,791,891; 6,777,757; 6,766,960; 6,700,151; 6,671,040; 6,667,902; and 6,650,143, all of which are incorporated herein by reference in their entireties to the extent that such are not inconsistent with the other portions of present detailed description. Applicants have recognized that such permanent memory circuits may be resistant to gamma ray radiation, chemicals (e.g., peroxide) and/or high temperatures, and thus may be particularly suitable for use in manufacturing transponders for use in marking objects that will be subjected to the extremes of sterilization. The permanent memory type transponder may include a housing, shell or encapsulant. Such a permanent memory transponder may be particularly useful for marking gauze or sponges. Such a transponder may be attached to a medical procedure related object in any variety of fashions, including sewn to, sewn in, adhered via adhesives or heat or RF welding, riveted, tied to, via a snap, stapled, etc.

Various structures are referred to as shielded, that is shielded at least from certain radio frequencies or wavelengths and/or microwave frequencies or wavelength in the frequency ranges or wavelength ranges at which the wireless transponders and associated interrogators operate, i.e., frequency ranges or wavelength ranges of interrogation signals transmitted by the interrogators and/or frequency ranges or wavelength ranges of response signals returned by wireless transponders. The shield may be a Faraday cage, that sufficiently attenuates electromagnetic signals as to prevent communication between the interrogator(s) and the wireless transponder(s). The shield (e.g., Faraday cage) can comprise sheets and/or meshes of conductive material (e.g., aluminum, copper, silver, gold, mild steel), of sufficient conductivity, thickness, and geometry as to cause attenuation (e.g., 50 dB; 60 dB reduction via a silver coated nylon fabric; 85 dB reduction via aluminum foil, 120 dB reduction via Mu-copper foil of 0.12 mm thick) in the particular wavelength or frequency ranges of interest (e.g., 125 kHz, 13.5 MHz, 900 MHz, and 3.5-5.8 MHz). Where a mesh is employed, the holes or apertures of the mesh should have a characteristic dimension that is much smaller (e.g., ¼ wavelength) than the wavelength of the signal to be stopped (i.e., interrogation signal and/or response signal).

The above description of illustrated embodiments, including what is described in the Abstract, is not intended to be exhaustive or to limit the embodiments to the precise forms disclosed. Although specific embodiments of and examples are described herein for illustrative purposes, various equivalent modifications can be made without departing from the spirit and scope of the disclosure, as will be recognized by those skilled in the relevant art. The teachings provided herein of the various embodiments can be applied to other transponders and interrogation and detection systems, not necessarily the exemplary surgical object transponders and interrogation and detection systems generally described above.

Also for instance, many of the embodiments described herein, perform interrogation and detection of transponder tagged objects using multiple antennas. Successive ones of the antennas may be used to transmit an interrogation signal, while two or more antennas are monitored for a response to the interrogation signal. Such may provide significant advantages over more conventional methods, for example motion-based methods that employ motion (e.g., sweeping) of an antenna (e.g., wand) over a patient. For instance, this allows the transmit and receive paths to the transponder to be different from one another (e.g., the transmit path is from a first antenna to a transponder, while the receive path is from the transponder to a second antenna). Hence, the path length to the transponder may be shortened in many configurations, thus improving the signal. For instance, when using a single antenna to both transmit an interrogation signal and to receive a response to the interrogation signal, the power of the received signal is equal to about the 6th root of the input power. However, when using multiple antennas to transmit and receive over the same area, interrogation path length in one direction may be shorter. Another advantage is that all scan time may be averaged, allowing a longer noise time averaging (e.g., 10 seconds) as opposed to motion-based scanning, where integration time may be limited (e.g., about 0.25 seconds per sample). Even further, a representative value of noise samples measured over a plurality of antennas may be employed to determine noise to be removed from noise plus signals received at one of the antennas, thereby advantageously lowering a noise floor and/or increasing range or performance. Thus, the various disclosed embodiments may provide significantly better performance.

In some embodiments, a high speed LINUX-based microprocessor may be employed in the console. In some embodiments, an LCD touch screen may be employed as a user interface device. Some embodiments may include update-ready software images for new applications. Such may facilitate the automatic loading of instructions on detection of a new device. RF reading may be performed using a handheld wand, via antennas located at the various nursing stations, a standalone handheld RFID reader, and/or via antennas positioned to interrogate all or part of a body. A PDR log may be maintained. Information may be offloaded in a variety of fashions, for instance a memory stick, wireless data transfer, or printer. An optional monitor may be coupled to the presence/absence interrogator or reader to display video or other images. In some embodiment, one or more machine-readable symbol readers may be coupled to the presence/absence interrogator or reader to read machine-readable symbols and transfer read data to the console. In some embodiments, a reading or scanning device (e.g., handheld antenna, handheld RFID reader, machine-readable symbol readers, antenna position to reader items on various tables and stands or nursing stations) may be a USB device, which automatically uploads counting or accounting instructions (e.g., software) to a presence/absence interrogator or reader when communicatively coupled thereto. The reading or scanning device may be appropriate for use with aseptic techniques, for example via placement under a drape or otherwise covered, or having been sterilized (e.g., autoclave). The reader or scanning device may be an antenna suitable for interrogating RFID transponders or a reader suitable for interrogating RFID transponders. Such may be incorporated in a mat, dish, tray or packed coil apparatus. Such may be used as a check in and/check out apparatus to ensure management or accounting of objects in the medical procedure environment. A suitable antenna may be a coil that enables object reading in random orientations over specific portions of nurse management areas (e.g., instrument or supply tables or stands).

Also for instance, the foregoing detailed description has set forth various embodiments of the devices and/or processes via the use of block diagrams, schematics, and examples. Insofar as such block diagrams, schematics, and examples contain one or more functions and/or operations, it will be understood by those skilled in the art that each function and/or operation within such block diagrams, flowcharts, or examples can be implemented, individually and/or collectively, by a wide range of hardware, software, firmware, or virtually any combination thereof. In one embodiment, the present subject matter may be implemented via Application Specific Integrated Circuits (ASICs). However, those skilled in the art will recognize that the embodiments disclosed herein, in whole or in part, can be equivalently implemented in standard integrated circuits, as one or more computer programs running on one or more computers (e.g., as one or more programs running on one or more computer systems), as one or more programs running on one or more controllers (e.g., microcontrollers) as one or more programs running on one or more processors (e.g., microprocessors), as firmware, or as virtually any combination thereof, and that designing the circuitry and/or writing the code for the software and or firmware would be well within the skill of one of ordinary skill in the art in light of this disclosure.

Various exemplary methods or processes are described. It is noted that these exemplary methods or processes may include additional acts and/or may omit some acts. In some implementations, the acts of the various exemplary methods or processes may be performed in a different order and/or some acts may be executed or performed concurrently.

In addition, those skilled in the art will appreciate that the mechanisms of taught herein are capable of being distributed as a program product in a variety of forms, and that an illustrative embodiment applies equally regardless of the particular type of physical signal bearing media used to actually carry out the distribution. Examples of signal bearing media include, but are not limited to, the following: recordable type media such as floppy disks, hard disk drives, CD ROMs, digital tape, and computer memory.

The various embodiments described above can be combined to provide further embodiments. To the extent not inconsistent with the teachings herein, all U.S. patents, U.S. patent application publications, U.S. patent applications, foreign patents, foreign patent applications and non-patent publications commonly owned with this patent application and referred to in this specification and/or listed in the Application Data Sheet including: U.S. Pat. No. 6,026,818, issued Feb. 22, 2000; U.S. Patent Publication No. US 2004/0250819, published Dec. 16, 2004; U.S. Pat. No. 8,710,957, issued Apr. 29, 2014; U.S. Pat. No. 7,898,420, issued Mar. 1, 2011; U.S. Pat. No. 7,696,877, issued Apr. 13, 2010; U.S. Pat. No. 8,358,212, issued Jan. 22, 2013; U.S. Pat. No. 8,111,162, issued Feb. 7, 2012; U.S. Pat. No. 8,354,931, issued Jan. 15, 2013; U.S. Patent Publication No. US 2010/0108079, published May 6, 2010; U.S. Patent Publication No. US 2010/0109848, published May 6, 2010; U.S. Patent Publication No. US 2011/0004276, published Jan. 6, 2011; U.S. Patent Publication No. US 2011/0181394, published Jul. 28, 2011; U.S. Patent Publication No. US 2013/0016021, published Jan. 17, 2013; PCT Patent Publication No. WO 2015/152975, published Oct. 8, 2015; U.S. Provisional patent application Ser. No. 62/143,726 filed Apr. 6, 2015; U.S. Provisional patent application Ser. No. 62/182,294 filed Jun. 19, 2015; U.S. Provisional patent application Ser. No. 62/164,412 filed May 20, 2015; U.S. Non-Provisional patent application Ser. No. 14/523,089 filed Oct. 24, 2014; U.S. Non-Provisional patent application Ser. No. 14/327,208 filed Jul. 9, 2014; U.S. Non-Provisional patent application Ser. No. 15/003,515 filed Jan. 21, 2016; U.S. Non-Provisional patent application Ser. No. 15/003,524 filed Jan. 21, 2016; U.S. Non-Provisional Patent application Ser. No. 15/052,125 filed Feb. 24, 2016; U.S. Non-Provisional patent application Ser. No. 15/053,965 filed Feb. 25, 2016; U.S. Provisional patent application Ser. No. 62/360,864 filed Jul. 11, 2016 and entitled "METHOD AND APPARATUS TO ACCOUNT FOR TRANSPONDER TAGGED OBJECTS USED DURING CLINICAL PROCEDURES EMPLOYING A SHIELDED RECEPTACLE WITH ANTENNA" (now U.S. Patent Application Publication No. 2019-0290392); U.S. Provisional patent application Ser. No. 62/378,511 filed Aug. 23, 2016 and entitled "METHOD AND APPARATUS TO ACCOUNT FOR TRANSPONDER TAGGED OBJECTS USED DURING CLINICAL PROCEDURES, FOR EXAMPLE INCLUDING COUNT IN AND/OR COUNT OUT AND PRESENCE DETECTION" (now U.S. Patent Application Publication No. 2019-0388183); and U.S. Provisional patent application Ser. No. 62/648,534 filed Mar. 27, 2018 and entitled "METHOD AND APPARATUS TO ACCOUNT FOR TRANSPONDER TAGGED OBJECTS USED DURING CLINICAL PROCEDURES, EMPLOYING A TROCAR" (now U.S. Patent Application Publication No. 2019-0298478), are each incorporated herein by reference, in their entirety. Aspects of the embodiments can be modified, if necessary, to employ systems, circuits and concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A system to track items in a clinical environment, the system comprising:
a number of antennas, the antennas positioned and oriented in the clinical environment to provide coverage of at least a portion of the clinical environment;
at least one interrogator, the at least one interrogator communicatively coupled to the antennas and operable to cause the at least one antenna to emit at least one of radio or microwave frequency energy interrogation signals and to detect response signals from any exposed wireless communications transponders in the clinical environment;
at least one shielded receptacle in the clinical environment, the at least one shielded receptacle having an interior and at least one shield that shields the interior of the shielded receptacle and any wireless communications transponders in the interior from at least one of radio or microwave frequency energy emitted by the antennas, at least one the at least one shielded receptacle is in a closed configuration;
a plurality of tagged clinical procedure items, each of the tagged items clinical procedure items having a respective wireless communications transponder physically coupled thereto; and
at least one piece of packaging, the at least one piece of packaging having an interior and at least one shield that shields the interior of the packaging and any wireless communications transponders in the interior of the packaging from at least one of radio or microwave frequency energy emitted by the antennas while the at least one piece of packaging is sealed, wherein the at least one piece of packaging releasably retains a number of the tagged clinical procedure items prior to use of the tagged clinical procedure items,
wherein the tagged clinical procedure items are disposable pieces of gauze and at least one of the at least one piece of packaging contains at least two sterile tagged disposable pieces of gauze prior to opening of the respective piece of packaging and the at least one of the at least one piece of packaging is hermetically sealed prior to opening of the respective piece of packaging.

2. The system of claim 1 wherein at least one of the at least one piece of packaging comprises a disposable metal or metalized foil envelope.

3. The system of claim 1 wherein at least one of the at least one piece of packaging comprises a disposable or a re-sterilizable tray or tote.

4. The system of claim 1 wherein the plurality of tagged clinical procedure items includes a number of tagged disposable items, each of the tagged disposable items having a respective radio frequency identification (RFID) wireless communications transponder physically coupled thereto.

5. The system of claim 1 wherein the plurality of tagged clinical procedure items includes a number of tagged clinical procedure instruments, each of the tagged clinical procedure instruments having a respective radio frequency identification (RFID) wireless communications transponder physically coupled thereto.

6. A system to track items in a clinical environment, the system comprising:

a number of antennas, the antennas positioned and oriented in the clinical environment to provide coverage of at least a portion of the clinical environment;

at least one interrogator, the at least one interrogator communicatively coupled to the antennas and operable to cause the at least one antenna to emit at least one of radio or microwave frequency energy interrogation signals and to detect response signals from any exposed wireless communications transponders in the clinical environment;

at least one shielded receptacle in the clinical environment, the at least one shielded receptacle having an interior and at least one shield that shields the interior of the shielded receptacle and any wireless communications transponders in the interior from at least one of radio or microwave frequency energy emitted by the antennas, at least one the at least one shielded receptacle is in a closed configuration;

at least one processor, the at least one processor communicatively coupled to the at least one interrogator; and at least one nontransitory processor-readable medium that stores at least one of processor-executable instructions or data, execution of which causes the at least one processor to:

during a clinical procedure, determine whether the at least one antenna in the clinical environment detected any response signals from any wireless transponders in the clinical environment; and cause an alert to be provided in response to a determination that the at least one antenna detected at least one response signals from any wireless transponders in the clinical environment proximate the end of the clinical procedure.

7. The system of claim 6 wherein the at least one of processor-executable instructions or data, when executed cause the at least one processor to:
determine whether the at least one antenna in the clinical environment detected any response signals from any wireless transponders proximate the end of the clinical procedure without determining whether any wireless transponders are present in the shielded receptacle.

8. The system of claim 1 wherein the at least one shielded receptacle has a port that is selectively operable between the closed configuration and an open configuration, in the open configuration the port provides physical access to the interior of the shielded receptacle from an exterior thereof and in the closed configuration the port prevents physical access to the interior of the shielded receptacle from the exterior thereof.

9. The system of claim 8 wherein the port of the at least one shielded receptacle includes a cover selectively moveable between the closed configuration and the open configuration.

10. The system of claim 9 wherein the cover is biased into the closed configuration.

11. The system of claim 9 wherein the at least one antenna comprises a plurality of room antennas, positioned throughout the clinical environment, and oriented to provide coverage of substantially all unshielded portions of the clinical environment.

12. The system of claim 9 wherein the at least one antenna comprises a plurality of room antennas, the room antennas at respective fixed positions and orientations throughout the clinical environment to provide coverage of substantially all unshielded portions of the clinical environment.

13. The system of claim 9 wherein the at least one antenna comprises at least one handheld or body-worn antenna.

* * * * *